United States Patent [19]
Carson et al.

[11] Patent Number: 5,985,847
[45] Date of Patent: Nov. 16, 1999

[54] DEVICES FOR ADMINISTRATION OF NAKED POLYNUCLEOTIDES WHICH ENCODE BIOLOGICALLY ACTIVE PEPTIDES

[75] Inventors: Dennis A. Carson, Del Mar; Eyal Raz, San Diego, both of Calif.

[73] Assignee: The Regents of the University of California, Oakland, Calif.

[21] Appl. No.: 08/928,412

[22] Filed: Sep. 12, 1997

Related U.S. Application Data

[63] Continuation of application No. 08/464,879, Jun. 7, 1995, abandoned, which is a continuation-in-part of application No. 08/112,440, Aug. 26, 1993, abandoned.

[30] Foreign Application Priority Data

Aug. 25, 1994 [WO] WIPO ..................... PCT/US94/09661

[51] Int. Cl.$^6$ ........................... A61K 48/00; A61B 17/20
[52] U.S. Cl. .......................... 514/44; 435/285.1; 424/34; 424/278.1; 604/46
[58] Field of Search ............................... 514/44; 424/34; 424/278.1; 435/285.1; 604/46

[56] References Cited

U.S. PATENT DOCUMENTS

| | | | |
|---|---|---|---|
| 3,969,497 | 7/1976 | Kniker | 436/543 |
| 5,250,293 | 10/1993 | Gleich | 424/78.04 |
| 5,262,128 | 11/1993 | Leighton et al. | 422/100 |
| 5,580,859 | 12/1996 | Felgner et al. | 435/440 |
| 5,589,466 | 12/1996 | Felgner et al. | 435/440 |

FOREIGN PATENT DOCUMENTS

WO 90/11092   10/1990   WIPO .

OTHER PUBLICATIONS

Chien, "Mucosal Drug Delivery: Potential Routes for Non–invasive Systemic Administration," *Novel Drug Delivery Systems*, 50:197–228.
Chien, "Nasal Drug Delivery and Delivery Systems," *Novel Drug Delivery Systems*, 50:229–268.
Chien, "Transdermal Drug Delivery and Delivery Systems," *Novel Drug Delivery Systems*, 50:301–380.
Sloan, "Use of Solubility Parameters from Regular Solution Theory to Describe Partitioning–Driven Processes," *Prodrugs Topical and Ocular Drug Delivery*, 53:179–204.
Tice, et al., "Parenteral Drug Delivery: Injectables," *Treatise on Controlled Drug Delivery*, pp. 315–339, Marcel Dekker, New York.
Chang, et al., "Nasal Drug Delivery," *Treatise on Controlled Drug Delivery*, pp. 423–463, Marcel Dekker New York.
Been, et al., "One Binding Site Determines Sequence Specificity of Tetrahymena Pre–rRNA Self–Splicing, Trans–Splicing, and RNA Enzyme Activity," *Cell*, 47:207–216, Oct. 24, 1986.
Gillies, et al., "Expression of Human Anti–Tetanus Toxoid Antibody in Transfected Murine Myeloma Cells," *Bio/Technology*, 7:799–804, Aug. 1989.

Ward, et al., "Binding activities of a repertoire of single immunoglobulin variable domains secreted from *Escherichia coli*," *Nature*, 341:544–546, Oct. 12, 1989.
Wolff, et al., "Conditions Affecting Direct Gene Transfer into Rodent Muscle In Vivo," *BioTechniques*, 11:474–485 (1991).
Cohen, "Naked DNA Points Way to Vaccines," *Science*, 259:1691–1692, Mar. 19, 1993.
Acsadi, et al., "Human dystrophin expression in mdx mice after intramuscular injection of DNA constructs," *Nature*, 352:815–818, Aug. 29, 1991.
Wolff, et al., "Direct Gene Transfer into Mouse Muscle in Vivo," *Science*, pp. 1465–1468, Mar. 1990.
Barr, et al., "Systemic Delivery of Recombinant Proteins by Genetically Modified Myoblasts," *Science*, 254:1507–1512, Dec. 1991.
Ulmer, et al., "Heterologous Protection Against Influenza by Injection of DNA Encoding a Viral Protein," *Science*, 259:1745–1748, Mar. 19, 1993.
"The Ultimate Delivery System: Lectro Patch Offers Large Molecule, 8 Day Drug Delivery," General Medical Company (1991).
Kaplan, et al., "Rational Immunotherapy with Interleukin 2," *Bio/Technology*, 10:157–162, Feb. 1992.
Caligiuri, et al., "Selective Modulation of Human Natural Killer Cells In Vivo After Prolonged Infusion of Low Dose Recombinant Interleukin 2," *J. Clin. Invest.*, 91:123–132, Jan. 1993.
Teppler, et al., "Prolonged Immunostimulatory Effect of Low–Dose Polyethylene Glycol Interleukin 2 in Patients with Human Immunodeficiency Virus Type 1 Infection," *J. Exp. Med.*, 177:483–492, Feb. 1993.
Stribling, et al., "Aerosol gene delivery in vivo," *Proc. Natl. Acad. Sci. USA*, 89:11277–11281, Dec. 1992.
Hefeneider, et al., "In Vivo Interleukin 2 Administration Augments the Generation of Alloreactive Cytolytic T Lymphocytes and Resident Natural Killer Cells," *The Journal of Immunology*, 130:222–227, Jan. 1983.
Goldstein, et al., Repetitive Weekly Cycles of Interleukin 2: Effect of Outpatient Treatment with a Lower Dose of Interleukin 2 . . . , *Cancer Research*, 49:6832–6839, Dec. 1, 1989.
Robinson, et al., "Use of Direct DNA Inoculations to Elicit Protective Immune Responses," *Journal of Cellular Biochemistry*, Supplement 17D, pp. 85 and 92, Mar. 1993.
Donohue, et al., "In Vivo Administration of Purified Jurkat–derived Interleukin 2 in Mice," *Cancer Research*, 44:1380–1386, Apr. 1984.

(List continued on next page.)

*Primary Examiner*—James Ketter
*Attorney, Agent, or Firm*—Foley & Lardner; Stacy L. Taylor

[57] ABSTRACT

This invention relates to apparatus and compositions for administering antigens and immunostimulatory peptides to a mammalian host by the introduction of one or more naked polynucleotides to operatively encode for the antigens and immunostimulatory peptides, preferably by non-invasive means.

5 Claims, 20 Drawing Sheets

OTHER PUBLICATIONS

Lotz et al., "β Cell Stimulating Factor 2/Interleukin 6 is a Costimulant for Human Thymocytes . . . " *J. Exp. Med.*, 167:1253–1258, Mar. 1988.

Del Rey, et al., "Antidiabetic effects of interleukin 1," *Proc. Natl. Acad. Sci. USA*, 86:5943–5947, Aug. 1989.

Shields, et al., "Calorie restriction suppresses subgenomic mink cytapathic focus–forming murine leukemia virus transcription . . . " *Proc. Natl. Acad. Sci. USA*, 88:11138–11142, Dec. 1991.

Tang, et al., "Genetic immunization is a simple method for eliciting an immune response," *Nature*, 356:152–154, Mar. 12, 1992.

Krieg, et al., "Functional messenger RNAs are produced by SP6 in vitro transcription of cloned cDNAs," *Nucleic Acids Research*, 12:7057–7071, 1984.

Gorman, et al., "The Rous sarcoma virus long terminal repeat is a strong promoter when introduced into a variety of eukaryotic cells . . . " *Proc. Natl. Acad. Sci. USA*, 79:6777–6781, Nov. 1982.

Norton, et al., "Bacterial β–Galactosidase as a marker of Rous Sarcoma Virus Gene Expression and Replication," *Molecular and Cellular Biology*, 5:281–290, Feb. 1985.

Davis, et al., "Direct Gene Transfer into Skeletal Muscle In Vivo: Factors Affecting Efficiency of Transfer and Stability of Expression," *Human Gene Therapy*, 4:151–159 (1993).

Davis, et al., "Plasmid DNA Is Superior to Viral Vectors for Direct Gene Transfer into Adult Mouse Skeletal Muscle," *Human Gene Therapy*, 4:733–740 (1994).

DEVICES FOR ADMINISTRATION OF NAKED POLYNUCLEOTIDES WHICH ENCODE BIOLOGICALLY ACTIVE PEPTIDES

RELATED U.S. PATENT APPLICATIONS

This is a continuation of application Ser. No. 08/464,879, filed Jun. 7, 1995, now abandoned, which is a continuation-in-part of U.S. Ser. No. 08/112,440, filed in the United States Patent and Trademark Office on Aug. 26, 1993 now abandoned.

STATEMENT OF GOVERNMENT RIGHTS

This invention may have been made with Government support under Grant Nos. AR07567 and AR25443, awarded by the National Institutes of Health. The Government may have certain rights in this invention.

BACKGROUND OF THE INVENTION

1. Field of the Invention

This invention relates to methods for administering biologically active peptides to a mammalian host by the introduction thereto of one or more polynucleotides to operatively encode for the peptides, preferably by non-invasive means. It also relates to the administration of said polynucleotides to prevent and treat illnesses and loss of immune function associated with aging in mammals.

2. Description of Related Art

The direct introduction of a biologically active peptide or protein into the cells of a patient can have significant therapeutic value. However, this approach also has several drawbacks. Of primary concern is the risk of potential toxicities, particularly at dosages sufficient to produce a biological response to the peptide. From a practical perspective, there is also the problem of the cost associated with isolating and purifying or synthesizing the peptides. Moreover, the clinical impact of the peptides is also limited by their relatively short half-life in vivo which usually results from their degradation by any proteases present in the target tissue.

For these reasons, introduction of a protein into a patient by delivery of a gene which will express the protein in the patient/host is an intriguing alternative to administering the protein. However, to date the principal means for introduction of foreign genetic material into a host has involved the integration of the gene into the host genome by, for example, transforming the host's cells with a viral vector. Direct in vivo gene transfer into postnatal animals has also been reported using DNA encapsulated in liposomes including DNA entrapped in proteoliposomes containing viral envelope receptor proteins.

In 1984, work at the NIH was reported which showed that intrahepatic injection of naked, cloned plasmid DNA for squirrel hepatitis into squirrels produced both viral infection and the formation of antiviral antibodies in the squirrels (Seeger, et al., *Proc.Nat'l.Acad.Sci USA*, 81:5849–5852, 1984). Several years later, Feigner, et al., reported that they obtained expression of protein from "naked" polynucleotides (i.e., DNA or RNA not associated with liposomes or a viral expression vector) injected into skeletal muscle tissue (Felgner, et al., *Science*, 247:1465, 1990; see also, PCT application WO 90/11092). Felgner, et al. surmised that muscle cells efficiently take up and express polynucleotides because of the unique structure of muscle tissue, which is comprised of multinucleated cells, sarcoplasmic reticulum and a transverse tubular system which extends deep into the muscle cell.

Although it has been supposed that cells of other tissues may also be able to take up naked polynucleotides, expression in other tissues has only been identified to date when delivery of the expressed gene was via a delivery system, e.g., liposomal transformation of the cells. Indeed, other researchers have suggested that uptake and expression of naked polynucleotides in tissues other than skeletal musde does not occur at detectable or biologically active levels (see, e.g., Stribling, et al., *Proc. Natl. Acad. Sci. USA*, 89:11277–11281, 1992 [expression following aerosol delivery of a gene occurred with use of a liposomal delivery system but not with introduction of DNA alone]; and, Tang, et al., *Nature*, 356:152–154, 1992 [injection with a vaccine "gun" of an hGH plasmid coupled to colloidal gold beads into the skin of mice did not elicit an immune response]).

Although generally effective for gene expression within muscle cells, injection of DNA or RNA into muscle tissue for long-term therapy requires use of repeated injections to offset loss of expression from gene degradation. This approach may not only be time-consuming and expensive, but may also be impractical due to inflammation caused at and near the site of injection. Such inflammation can cause muscle or other somatic cells into which nucleotides are introduced to be themselves targeted by an immune response (see, e.g., Example I) and can lead to severe myonecrosis. Further, intramuscular injection of DNA not only risks injury to muscle tissue, but that injury apparently also compromises the efficacy of the therapy. For example, researchers working with the University of Ottawa recently observed that "[s]triated muscle is the only tissue found to be capable of taking up and expressing reporter genes that are transferred in the form of plasmid DNA . . . but our findings indicate that fibers damaged by the injection procedure do not take up and express plasmid DNA." (Davis, et al., *Human Gene Therapy*, 4:151–159, 1993).

Further, while use of intramuscular injections may be effective on at least a short term basis in therapies directed to disease in the muscle tissue itself, it is likely to be less effective in stimulating a tissue specific immune or other biological response to the expressed peptide elsewhere in the patient's body.

As a result, intramuscular injection is not a particularly viable route for achieving expression of peptides at the primary entry points for many infections; i.e., skin and mucosa.

Further, it appears that intramuscular injections of polynucleotides will lead to the formation of both antibodies and cytotoxic T cells in the tissue, due to release of any encoded protein by targeted muscle cells. In contrast, injection of protein (e.g., in a vaccination scheme) does not usually induce cytotoxic T cell formation because exogenous proteins do not efficiently enter the class I processing pathway.

In PCT application WO 90/11092 (discussed supra), the inventors propose tbat the injection of naked DNA into skeletal muscle or other somatic issues will lead to direct gene expression in the cytoplasm of the injected cells. The inventors further suppose that the encoded protien will then enter the class I processing pathway to induce cytotoxic T cell formation (which are necessary for the control of established viral infections and cancers). However, as discussed above, it appears that instead any somatic cell that expresses antigen must first release the antigen into the extracellular space for uptake by antigen presenting cells before a class I restricted cytotoxic T cell response can to the antigen can be induced. This conclusion is supported by recent research regarding antigen presentation where the observation was made that "the priming of an immune response against . . . class I restricted antigen that is expressed exclusively in non-hematopoietic cells invovlves the transfer of that antigen to a host bone marrow derived cell before its presentation." (Huang, et al., *Science*, 264:961–965, 1994). Thus, at least one premise on which the method for introduction of genetic material into muscle cells for protein expression of PCT application WO 90/11092 was based may not be accurate.

Use of intramuscular injections can, however, produce relatively high levels of protein expression systemically prior to degradation of the injected gene. While this response is desirable in therapies where protein replacement is the goal, it can lead to unintended toxicities in immunization protocols where relatively rapid clearance or lower levels of expression are optimal. As a result, introduction of the gene into tissues which regularly shed or regenerate (such as skin) and/or into cells with a relatively high attrition rate in vivo (such as antigen presenting cells) would be more useful routes for gene immunization.

With respect to delivery systems for genes, means such as viral vectors which introduce the gene into the host's genome present potential health risks association with damage to the genetic material in the host cell. Use of cationic liposomes or a biolistic device (i.e., a vaccine "gun" which "shoots" polynucleotides coupled to beads into tissue) to deliver genes in vivo is preparation intensive and requires some experimentation to select proper particle sizes for transmission into target cells. Further, any invasive means of introducing nucleotides (e.g., injection) poses problems of tissue trauma (particularly in long-term therapies) and presents limited access to certain target tissues, such as organs.

Means for non-invasive delivery of pharmaceutical preparations of peptides, such as iontophoresis and other means for transdermal transmission, have at least the advantage of minimizing tissue trauma. However, it is believed that the bioavailability of peptides following transdermal or mucosal transmission is limited by the relatively high concentration of proteases in these tissues. Yet unfortunately, reliable means of delivering peptides by transdermal or mucosal transmission of genes encoding for them has been unavailable.

The potential benefits of successful administration of peptides via in vivo expression of naked genes can be illustrated by comparison to the present state of immunotherapy wherein cytokine proteins (such as interleukin-2, hereafter "IL-2") are administered to a patient to treat or prevent diseases associated with aging.

Certain diseases occur as part of the aging process in virtually all mammalian species, despite differing life styles and life spans among those species. These diseases include cancer, hypertension, vascular diseases and insulin resistance that can result in diabetes. Because the timing of the onset of these diseases cannot be solely attributed to environmental factors, it has been assumed that their onset is genetically programmed. However, the processes which actually control the aging process and the incidence of age-associated illnesses are not known.

In general, aging is associated with a reduced ability to mount an immune response to exogenous antigens, a decreased functional reserve and response to stress, as well as an increased tendency toward fibrosis. All of these states are contributed to or controlled in part in vivo by circulating cytokines.

For example, interleukin-1 (IL-1) proteins affect glucose homeostasis and can act as a hypoglycemic agent in insulin resistant C57BL/Ks db mice and C57BL/6G ob/ob mice (Del Rey, et al., *Proc. Natl. Acad. Sci., USA*, 86:5943, 1989). In these animal models of adult onset diabetes, a single injection of human recombinant IL-1 normalized glucose blood levels for several hours. IL-1 is also known to exert effects on the hypothalamic-pituitary axis that influences appetite, and the response to stress. Thus, abnormalities in IL-1 production or responsiveness could underlie both non-insulin dependent diabetes and obesity in aging. IL-1 gene therapy (administered exactly as described for IL-2) may, therefore, prevent the onset of diabetes in mice and humans.

High blood pressure is another concomitant of aging that is frequently associated with diabetes. Recent experiments have shown that a major regulator of blood pressure is the endothelium-derived relaxing factor, nitric oxide. The production of nitric oxide is regulated by IL-1. Hence, the increase in blood pressure that occurs with aging may also be prevented by IL-1 gene therapy. IL-1 protein induces fever and even shock when administered acutely to animals. However, the continuous production of low levels of IL-1 following somatic gene therapy will avoid these side effects.

The biological effects of administering pharmaceutical doses of cytokine proteins have been explored recently by researchers seeking to stimulate the immune system to augment its response to certain pathogens and to maintain immune function in immunodeficient patients, such as those infected with human immunodeficiency virus (HIV).

Specifically, efforts to administer IL-2 as a therapeutic in immune system diseases have been recently reported by Teppler, et al., *J. Exp. Med.*, 177:483–492, 1993, (administration of recombinant IL-2 protein conjugates of polyethylene glycol to HIV infected patients); Caligiuri, et al., *J. Clin. Invest.*, 91:123–132, 1993, (prolonged infusions of recombinant IL-2 protein to patients with advanced cancers), and Kaplan, et al., i Bio/Technology 10:157–162, 1992, (administration of IL-2 to patients infected with *M. leprae* or HIV). The focus of these studies has been to develop means of administering the IL-2 protein in a way which will minimize its toxicity.

Toxicity of the IL-2 protein has been a major impediment to its use as an effective therapeutic. To be effective, IL-2 therapy generally requires that the administered protein be present in serum in sufficient quantity to saturate high affinity IL-2 receptors and induce marked expansion of circulating natural killer (NK) cells. With high doses of IL-2, however, come life-threatening toxicities such as severe hypotension, pulmonary edema, renal failure, cardiac arrhythmias and neurologic disfunction.

The approach taken by the above-referenced researchers to overcome this problem has been to experiment with prolonged administration of IL-2 protein at relatively low doses after the onset of infection and/or disease. This approach, however, has yet to define effective parameters for consistent, predictable IL-2 therapy. In particular, the levels of circulating protein resulting from introduction of cytokines vary substantially over time, in part due to protease degradation. Repeated injections are, therefore, required with resulting "hills and valleys" in the quantity of protein available to the patient. Moreover, the work with IL-2 does not indicate whether a similar approach would, even after substantial clinical experimentation, prove effective for use with other cytokines which play roles in various disease states, including age-associated illnesses.

A need, therefore, exists for an efficient means of introducing a protein (including but not limited to cytokines and antigens) into a host in a manner which will minimize the toxicity of the protein. More specifically, a need also exists for a means for introducing a protein into a host in a manner which will produce a consistent but subtherapeutic level of protein expression over a long period of time. In the latter respect, a need particularly exists for a means of administering cytokines to prevent as well as treat age-associated illnesses.

More generally, the above discussion also illustrates the need for an effective means of introducing naked nucleotides which will express in vivo a peptide which can induce local immunity in skin and mucosa to vaccinate a host against, for example, sexually transmitted diseases and respiratory illnesses.

It also suggests a need for a means of introducing a gene encoding for a biologically active peptide to a host in a tissue-specific manner without significant tissue trauma.

The present invention addresses all of these needs.

SUMMARY OF THE INVENTION

The details of the preferred embodiment of the present invention are set forth in the accompanying drawings and the description below. Once the details of the invention are known, numerous additional innovations and changes will become obvious to one skilled in the art.

1. DEFINITIONS

The following definitions are provided to simplify discussion of the invention. Those skilled in the art will, however, recognize that these definitions may be expanded to include equivalents without departing from the legitimate scope or spirit of the invention. For this reason, these definitions should not be construed as limiting the invention.

a. "Naked polynucleotide(s)" refers to DNA or RNA and can include sense and antisense strands as appropriate to the goals of the therapy practiced according to the invention. Polynucleotide in this context may include oligonucleotides. Naked in this context means polynucleotides which are not complexed to colloidal materials (including liposomal preparations), or contained within a vector which would cause integration of the polynucleotide into the host genome.

b. "Operatively encoding" refers to a polynucleotide which has been modified to include promoter and other sequences necessary for expression and, where desired, secretion of the desired translation product; e.g., a peptide or protein. All the embodiments of the invention can be practiced using known plasmid expression vectors. Preferably, these vectors will include cDNA ('s) which encode for the desired translation product. Therefore, unless context otherwise requires, it will be assumed that "polynucleotide" or "naked polynucleotide" refers to operatively encoding sequences contained in a suitable plasmid expression vector, examples of which are provided herein.

c. "Mixture of polynucleotides" shall refer to more than one and up to 200 polynucleotide species which are under the control of the same promoter.

d. "Synthesis" refers to well-known means of synthesizing polynucleotide sequences and may include isolation and purification of native polynucleotides.

e. "Peptide" refers to small peptides, polypeptides, oligopeptdes and proteins which have a desired biological effect in vivo.

f. "Iontophoresis" refers to a known means of transdermal transmission presently used to deliver peptides continuously to a host. More specifically, it is a process that facilitates the transport of ionic species by the application of a physiologically acceptable electrical current. This process and other transdermal transmission means are described in Chien, et al. *Transdermal Drug Delivery*, "Novel Drug Delivery Systems", Ch. 7, part C, (Marcel Dekker, 1992), the relevant disclosures of which are incorporated herein by this reference for the purpose of illustrating the state of knowledge in the art concerning techniques for drug delivery.

g. "Detergents/Absorption Promoters" refers to chemical agents which are presently known in the art to facilitate absorption and transfection of certain small molecules, as well as peptides.

h. "Antigen Presenting Cells", or "APC's" include known APC's such as Langerhans cells, veiled cells of afferent lymphatics, dendritic cells and interdigitating cells of lymphoid organs. The definition also includes mononuclear cells such as (1) lymphocytes and macrophages which take up and express polynucleotides according to the invention in skin and (2) mononuclear cells depicted on histological photographs contained herein. These cells are not tissue cells but are likely to be antigen presenting cells. The most important of these with respect to the present invention are those APC's which are known to be present in high numbers in epithelia and thymus dependent areas of the lymphoid tissues, including epidermis and the squamous mucosal epithelia of the buccal mucosa, vagina, cervix and esophagus (areas with "relatively high" concentrations of APC's). In addition to their definitions set forth below, therefore, "skin" and "mucosa" as used herein particularly refer to these sites of concentration of APC's.

i. "Host" refers to the recipient of the therapy to be practiced according to the invention. The host may be any vertebrate, but will preferably be a mammal. If a mammal, the host will preferably be a human, but may also be a domestic livestock or pet animal.

j. "Target tissue" refers to the tissue of the host in which expression of the naked polynucleotide is sought.

k. "Skin" as used herein refers to the epidermal, dermal and subcutaneous tissues of a host.

l. "Mucosa" refers to mucosal tissues of a host wherever they may be located in the body including, but not limited to, respiratory passages (including bronchial passages, lung epithelia and nasal epithelia), genital passages (including vaginal, penile and anal mucosa), urinary passages (e.g., urethra, bladder), the mouth, eyes and vocal cords.

m. "Point of Entry" refers to the site of introduction of the naked polynudeotide into a host, including immediately adjacent tissue.

n. "Surrogate End Point" refers to a biological state of the host occurring just prior to the onset of disease. Examples include loss of glucose tolerance (diabetes), increased cholesterol levels (heart disease) and the presence of free radical amino acids in blood and urine (indicates loss of free radical detoxifying enzymes in the central nervous system).

o. "Biological Impairment" refers to a loss of immune function or wellness (including disease and impairment of the host's resistance to disease) which is associated with aging in mammals.

p. "Subtherapeutic Levels" and "Subtherapeutic Dosage" refer to expression of a peptide by a naked polynucleotide in a host in a quantity which is not sufficient to invoke an acute, detectable response by the host to the expressed peptide following a single noncumulative administration to the host of the naked polynucleotide.

q. "Dermal" and "Epidermal Administration" mean routes of administration which apply the naked polynucleotide(s) to or through skin. Dermal routes include intradermal and subcutaneous injections as well as transdermal transmission. Epidermal routes include any means of irritating the outermost layers of skin sufficiently to provoke an immune response to the irritant. The irritant may be a mechanical or chemical (preferably topical) agent.

r. "Epithelial Administration" involves essentially the same method as chemical epidermal administration, except that the chemical irritant is applied to mucosal epithelium.

s. "IL" refers to interleukin.

t. "TH1 Response(s)" refers to a cellular immune response that is induced preferentially by antigens that bind to and activate certain APC's; i.e., macrophages and dendritic cells.

u. "Biologically Active Peptide(s)" refers to a peptide which, when administered to a host, exerts a therapeutic benefit or induces an immune response therein.

2. DISCUSSION

In one aspect, the invention consists of means of inducing local immunity to an antigen or a systemic response to a therapeutic peptide or polynucleotide by delivering a naked polynucleotide to a host's cells which operatively encodes the antigen or peptide. More particularly, the naked polynucleotide is preferably delivered to a tissue which contains a relatively high concentration of antigen presenting cells as compared to other tissues of the body. Although it is not intended that the invention will be entirely limited by a particular theory as to the mechanism of expression involved, it is believed that a biological response in these tissues following administration of the naked polynucleotide is achieved because the polynucleotide is expressed by mononuclear cells, most likely the host's antigen presenting cells. It is also believed that the mononuclear cells are involved in an inflammatory immune response to the introduction of the naked polynucleotide.

Based on histological studies, the naked polynucleotides do not appear to be taken up directly by fibroblasts or other tissue cells in significant quantities (see, Example 9 and FIG. 15). This conclusion is borne out by studies showing that (1) intradermal administration of even minute amounts of naked polynucleotides into mice induced a prominent TH1 response (indicative of antigen presentation by macrophages and dendritic cells; see, Example 17 and FIGS. 24–25); (2) intradermal administration of naked polynucleotide to mice induced the formation of cytotoxic T cells without stimulating production of detectable levels of antibody (see, Example 15 and FIG. 21); and, (3) induction of prolonged immunological memory with respect to the polynucleotide as an antigen (Example 16 and FIGS. 22–23).

Given the apparent role of inflammation in this method of the invention, it will also be appreciated by those of skill in the art that increased permeability in cell membranes of the target tissue associated with inflammation may enhance uptake of the naked polynucleotides (particularly across barriers such as skin and mucosa).

Ideally, the target tissue will be skin or mucosa. These tissues are particularly preferred when the therapy is directed to infections or diseases where it is desirable to induce a localized therapeutic or immune response. For example, a mucosal route of administration would be preferred for treatment of sexually transmitted diseases, where the therapy was directed to boosting the immune response to antigens in infected tissues. A nasal route of administration (via inhalation or insufflation) would also be of particular use in therapies directed toward treatment of respiratory and related diseases. Further, a mucosal or dermal route would be useful in immunizing against allergens. These tissue are also preferred for their regenerative ability, which limits the length of time that introduced materials will remain at the point of entry.

Because the antigen presenting cells present in the target tissue may serve to mediate the expression of the naked polynucelotide, the method of the invention may not be as useful for inducing systemic responses to the expressed peptide as it is for inducing a localized response. However, at sufficient dosage levels a transitory systemic effect can be induced. A useful application of this aspect of the invention for induction of systemic responses to the expressed peptide may, therefore, be as an adjuvant for other systemic therapies.

In another aspect of the invention, the APC's serve as vehicles to deliver the naked polynucelotide to lymphatic organs and to mucosal tissues other than those at the point of entry. This embodiment is illustrated by reference to the following hypothesis; the mechanism described should not, however, be construed as limiting the invention.

In this embodiment, it is believed that the APC's take up the naked polynucelotide at or near the point of entry then carry them into lymphatic circulation. Once at a lymph node, the APC will present the expressed protein as an antigen, thereby stimulating an immune response. From there, those APC's which carry "homing" receptors for, e.g., mucosa, may reenter lymphatic circulation until they settle in a target tissue other than the tissue at the point of entry. Where desired, homing receptors (specific membrane proteins which bind to target cell ligands) may be sequenced and incorporated into the naked polynucleotide.

With respect to expression in the lymph system, this embodiment also provides a means of enhancing the host's immune responsiveness by delivering cytokines to increase the concentration of specific cytokines present in the host. Particularly in the lymphatic organs, increases in the host's levels of circulating cytokines (administered with or shortly after antigen challenge) can boost the host's immune response to pathogenic antigens and (1) serve as an adjuvant for vaccines, (2) decrease the immune response to self-antigens in autoimmune diseases, or (3) decrease the immune response to alloantigens (produced, for example, following tissue or organ transplantation).

Where the APC's carrying the gene of interest migrate out of lymph nodes and circulate to tissues for which they have a homing receptor, the gene can be administered at an accessible point of entry for expression at a less convenient or accessible site. For example, a naked polynucelotide delivered intranasally may, under appropriate conditions, be expressed in the genital mucosa.

Another use for the invention would be in moderating an allergic response to an antigen. The nasal route of administration is of particular use in this regard.

For example, genes for IL-2, gamma interferon and/or transforming growth factor (TGFβ) could be administered to suppress production of IgE molecules. This approach is of particular interest because, in recent clinical trials, IL-2 and gamma interferon have proved toxic at dosages sufficient to interfere with production of IgE. In addition, because IgE molecules are predominately present in skin and mucosa, use of these routes as points of entry according to the invention can be expected to be particularly effective in moderating allergic responses in these tissues.

Examples where it would be useful to induce a localized response in skin or mucosa are extant. In particular, a mucosal route of administration would be preferred for treatment of sexually transmitted diseases. The therapy can be directed toward modulating the local immune response to an infectious agent such as HIV, human papillomae viruses (such as those responsible for causing genital warts), or to cutanaceous viral infections. Also, where immunosuppresion is of therapeutic value, gene(s) operatively encoding for immunosuppressive agents (such as TGFβ) could also be supplied according to the method of the invention. An example where this approach would be useful is in the treatment of inflammatory bowel disease.

One particularly useful aspect of the invention is its use to supply cytokines and biochemicals relevant to the incidence of illnesses associated with aging to the host at subtherapeutic levels for a prolonged period of time. In this aspect, the naked polynucleotide will operatively encode for a protein such as a cytokine or related growth factor whose presence or absence in mammalian circulation impacts the immune system in ways that facilitate or retard the development of illnesses associated with aging. Such illnesses may be retarded by enhancing levels of proteins whose concentrations in sera normally decrease with age, such as cytokines, growth hormones and enzymes (e.g., human α-L fucosidase, which can mediate inflammatory responses to antigens).

Another particular advantage of the invention is that it involves the administration of relatively minute doses of antigen. More specifically, because a polynucleotide that will operatively encode for an antigen is administered in lieu of the antigen itself, the quantity of foreign material being introduced to the host is relatively minimal. Moreover, routes of administration of naked polynucleotides through skin or mucosa require a lower concentration of DNA to produce the same magnitude of immune response than does the intramuscular route of administration (e.g., about 10–50 fold lower; see, e.g., Example 16 and FIGS. 22–23). As a result, the invention lends itself well to the administration of naked polynucleotides which encode for up to several hundred different antigens for use, as an example, as a polyvalent vaccine.

Another particular advantage of the invention will be its use in antisense therapy. Briefly, where a particular disorder is associated with the expression of a particular mutated nucleic acid sequence, a nucleotide sequence that interferes with the specific expression of the mutated gene at the transcriptional or translational level can be used. This approach utilizes, for example, antisense oligonucleotides and/or ribozymes to block transcription or translation of a specific mutated mRNA, either by masking that mRNA with an antisense nucleic acid or by cleaving it with a ribozyme.

Antisense nucleic acids are DNA or RNA molecules that are complementary to at least a portion of a specific mRNA molecule (Weintraub, *Scientific American*, 262:40, 1990). To date, several genes and oncogenes have been targeted for suppression or down-regulation including, but not limited to, p53 (V. S. Prasolov et al., *Mol. Biol. (Moscow)* 22:1105–1112, 1988); ras (S. K. Anderson et al., *Mol. Immunol.* 26:985–991, 1989; D. Brown et al., *Oncogene Res.* 4:243–249, 1989); fos (B. Levi et al., *Cell. Differ. Dev.* 25 (Suppl):95–102, 1988; D. Mercola et al., *Gene* 72:253–265, 1988); and myc (S. O. Freytag, *Mol. Cell. Biol.* 8:1614–1624, 1988; E. V. Prochownik et al., *Mol. Cell. Biol.* 8:3683–3695, 1988; S. L. Loke et al., *Curr. Top. Microbiol. Immunol.* 141:282–288, 1988).

It is not sufficient in all cases to block production of the target mutant gene. As described in Levine, et al., (*Biochimica et Biophisice Acta.*, 1032:119–136, 1990), there are at least five types of mutations that can contribute to the tumor phenotype. As a result, each mutation of a multiple mutation gene disorder must be targeted to optimize the benefits of antisense therapy. Because the method of the invention is particularly suited for delivery of a mixture of polynucleotides, it will be especially useful in multiple mutation antisense therapy.

Antisense therapy can also be used to block production of mutant proteins that act directly to increase the probability of producing neoplastic cells, such as in the Type III, Type IV and Type V mutations that mimic Type III described by Levine, et al., supra. Antisense polynucleotides are also therapeutically effective when mutation is not dominant, for instance when a non-mutant allele remains that encodes the proper protein. However, when the mutation is dominant, as in Type I mutations, and in cases wherein either both alleles are deleted or one is deleted and the other is mutant, as in certain Type III mutations, antisense therapy is preferably accompanied by replacement therapy.

In replacement therapy, a wild type gene is introduced into the target cells identified as having a mutant gene or protooncogene which results in production of the wild type protein necessary to forestall development of the disorder or neoplasia associated with the identified mutant gene(s).

In the case of tumor suppressor genes, it is known that introducing a suppressor gene into cultured cells either causes cell death or causes no discernible changes, however, the cells may no longer be tumorigenic in animals. Thus, in cases where ribozyme and/or antisense therapy is accompanied by gene replacement therapy, the chances are increased that the cell population containing the mutant gene for which the ribozyme or antisense oligonucleotide is specific will no longer contribute to development of neoplasia in the subject being treated.

The present invention also provides gene therapy for the treatment of cancer conditions; i.e., cell proliferative disorders that are mediated by a deletion of, or polymorphism in, a particular gene. Such therapy would achieve its effect by introduction of the specific antisense polynucleotide and/or replacement wild type gene into cells identified by the methods of this invention as having the proliferative disorder caused by mutated genes. Whether the cell will require replacement of the wild type gene as well as antisense therapy to prevent replication of a gene bearing a polymprphism must be determined on a case by case basis and will depend upon whether the mutation has a dominant effect, ie., whether both alleles of the wild type gene have been destroyed so that total absence of the gene has a cell proliferative effect.

The preferred routes of administration for inducing local immunity in or near the skin will be by transdermal transmission, intradermal injection or superficially scratching or irritating the outermost layer of epidermal cells (i.e., epidermal administration), although subcutaneous injection may also be of use in certain applications. The preferred routes of administraon for inducing local immunity in the respiratory tract will be by inhalation or insufflation; routes of administration to other mucosal tissues will vary according to their location.

Where the naked polynucieotides are to be introduced into skin or mucosa, delivery of the polynucleotide is preferably facilitated without need for injection by use of detergents, absorption promoters, chemical irritants (such as keratinolytic agents), or mechanical irritants. Detergents and absorption promoters which facilitate uptake of small molecules other than genes are well known in the art and may, without undue experimentation, be adapted for use in facilitating uptake of genes. Another substantially noninvasive approach to introducing the naked polynucleotides is by transdermal transmission (preferably iontophoresis) which has been used with success for transdermal transmission of peptides.

For those embodiments of the invention which involve stimulating production of cytokines and related peptdes in circulation, use of any parenteral route of administration is possible, although use of routes involving little or no invasion of host tissues are greatly preferred. However, because of the need for repeated administration of the naked polynucleotide(s), intramuscular injections are not preferred. Instead, introduction of the naked polynucleotide(s) to an area of the body which is regenerative, such as skin and mucosa, is preferred for their ability to replace cells which have been directly affected by trauma associated with each dosage. To ensure secretion of the proteins to be expressed in these embodiments of the invention, sequences controlling secretion known to those skilled in the art will be included in the administered naked polynudeotide, if not already present in the full-length gene.

Further, it should be noted that for use in the embodiments of the invention involving delivering peptides at subtherapeutic levels, the polynucdeotide may be conjugated to a liposome or delivered in cells which have been transfected in vitro with the polynucleotide. Nonetheless, for the reasons discussed above, use of a naked polynucleotide and a mucosal or dermal route of administration in these embodiments is still preferred. In particular, use of liposomes is likely to result in reduced levels of expression. This phenomenon is likely to be the result of impaired recognition by APC's of a liposome as an antigenic material.

BRIEF DESCRIPTION OF THE DRAWINGS

FIG. 2B depicts the results of an ELISA for anti-NP IgG in serum following intramuscular injection of naked pCMVRNP.

FIGS. 21A–24D depict the levels of cytotoxic T cells detected in mice after injection of various naked plasmids administered by intradermal injection.

FIG. 22 depicts the results of an EUSA for anti-β-galactosidase antibodies after administation of (1) a polynucleotide encoding the enzyme by intramuscular or intradermal injection, and (2) the enzyme by intradermal injection.

FIG. 23 depicts the results of an ELISA for anti-β-galactosidase antibodies in sera from the mice described with respect to FIG. 22 after a booster injection of antigen.

FIG. 24 depicts the results of an ELISA for IgG 2A type antibodies in sera for mice (1) injected intradermally or intramuscularly with a polynucleotide encoding β-galactosidase, or (2) the enzyme by intradermal injection.

DETAILED DESCRIPTION OF THE INVENTION

Figure 1A:
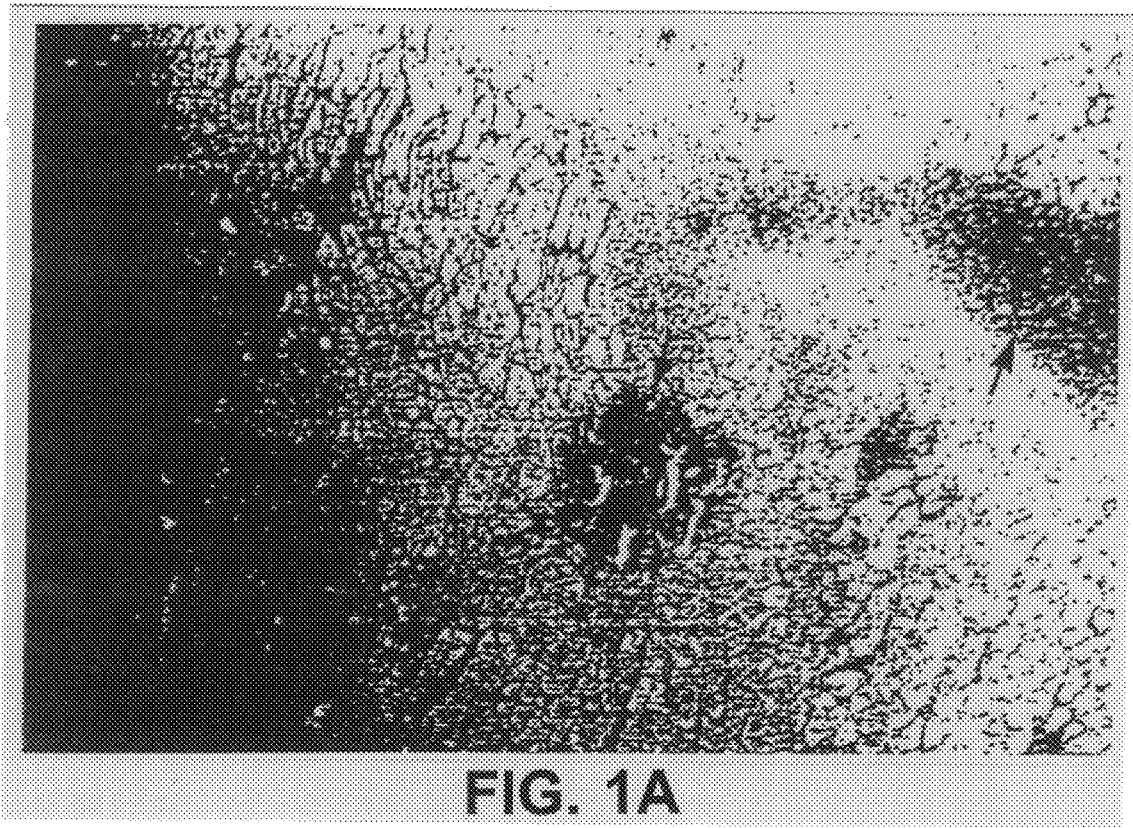
FIGS. 1a–1c depict sections of muscle tissue demonstrating chronic inflammation (panel A) and myonecrosis (panel B) following intramuscular injections of pREVk3 and pRSVIL-2. Panel C depicts sections of similar muscle tissue following subcutaneous injections of pREVK3 or pRSVIL-2.
Figure 1B:
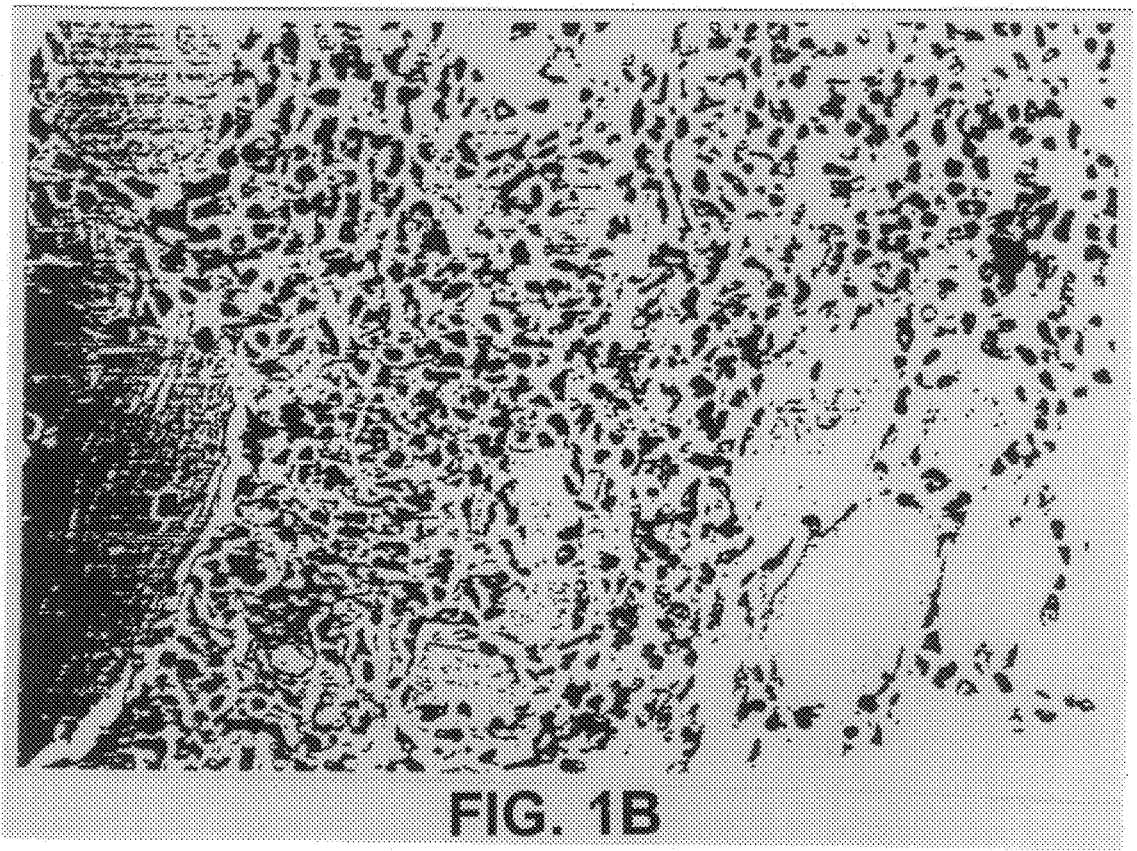

Throughout this description, the preferred embodiment and examples shown should be considered as exemplars, rather than limitations on the invention.

I. Introduction of Naked Polynucleotides into Target Tissues Having Substantial Concentrations of Antigen Presenting Cells A. Preparation of Naked Polynuclootides.

The polynucleotides to be used in the invention may be DNA or RNA, but will preferably be a complementary DNA (cDNA) sequence. The polynucleotide sequences used in the invention must be (a) expressible and (b) either non-replicating or engineered by means well known in the art so as not to replicate into the host genome. Illustrations of the preparation of polynucleotides suitable for use in the invention follow and specific examples showing how particular polynucleotide compositions were made are provided infra. It will, however, be apparent to those skilled in the art that other known means of preparing nonreplicating polynucleotides may also be suitable.

Polynucleotides for use in the invention can be obtained using hybridizaton methods well known in the art. DNA and RNA may also be synthesized using automated nucleic acid synthesis equipment well known in the art. Use of the well-known polymerase chain reaction (PCR) is particularly preferred for generating mixtures of polynucleotides. Genomic nucleic acids may be prepared by means well-known in the art such as the protocols described in Ausubel, et al., *Current Protocols in Molecular Biology*, Chs. 2 and 4 (Wiley Interscience, 1989). cDNA can be synthesized according to means well known in the art (see, e.g., Maniatis, et al., *Molecular Cloning*; A Laboratory Manual (Cold Spring Harbor Lab, New York, 1982). A cDNA expression library containing polynucleotides of interest can also be screened by means well known in the art. For reference, examples of such means are illustrated by the discussion below.

Preferred polynucleotides for use in specific applications are suggested in the preceding Summary of the Invention. For example, the naked polynucleotides may operatively encode for therapeutic peptides, but will preferably encode for immunogenic peptides which can act as antigens to provoke a humoral and/or cellular response. The naked polynucleotides can also operatively encode for an antibody. In this regard, the term "antibody" encompasses whole immunoglobulin of any class, chimeric antibodies, hybrid antibodies with dual or multiple antigen specificities and fragments including hybrid fragments. Also included within the meaning of "antibody" are conjugates of such fragments, and so-called antigen binding proteins (single chain antibodies) as described, for example, in U.S. Pat. No. 4,704,692. Alternatively, the encoded antibodies can be anti-idiotypic antibodies (antibodies that bind other antibodies) as described, for example, in U.S. Pat. No. 4,699,880.

Those of skill in the art will, however, appreciated that the methods of the invention may be adapted for use in administering any polynucleotide or mixture thereof which operatively encode therapeutic and/or immunogenic peptides of interest. The invention is therefore not limited to use with any particular polynucleotide(s).

As used herein, "polynucleotide" refers to a polymer of deoxyribonucleotides or ribonucleotides, in the form of a separate fragment or as a component of a larger construct. DNA encoding an therapeutic and/or immunogenic peptide of the invention can be assembled from cDNA fragments or from oligonucleotides which provide a synthetic gene which is capable of being expressed in a recombinant transcriptional unit. Polynucleotide sequences of the invention include DNA, RNA and cDNA sequences. A polynucleotide sequence can be deduced from the genetic code, however, the degeneracy of the code must be taken into account. Polynucleotides of the invention include sequences which are degenerate as a result of the genetic code, which sequences may be readily determined by those of ordinary skill in the art.

Polynucleotide sequences encoding a desired therapeutic and/or immunogenic peptide can be expressed in either eukaryotes or prokaryotes. Hosts can include microbial, yeast, insect and mammalian organisms. Methods of expressing DNA sequences having eukaryotic or viral sequences in prokaryotes are well known in the art. Biologically functional viral and plasmid DNA vectors capable of expression and replication in a host are also well known in the art. Such vectors are used to incorporate DNA of the invention.

Polynucleotides of the invention include functional derivatives of known polynucleotides which operatively encode for a therapeutic and/or immunogenic peptide of interest. By "functional derivative" is meant the "fragments," "variants," "analogs," or "chemical derivatives" of a molecule. A "fragment" of a molecule, such as any of the DNA sequences of the present invention, includes any nucleotide subset of the molecule. A "variant" of such molecule refers to a naturally occurring molecule substantially similar to either the entire molecule, or a fragment thereof. An "analog" of a molecule refers to a non-natural molecule substantially similar to either the entire molecule or a fragment thereof.

As used herein, a molecule is said to be a "chemical dervative" of another molecule when it contains additional chemical moieties not normally a part of the molecule. Such moieties may improve the molecule's solubility, absorption, biological half-life, etc. The moieties may alternatively decrease the toxicity of the molecule, eliminate or attenuate any undesirable side effect of the molecule, etc. Moieties which are known in the art to be capable of mediating such effects are disclosed, for example, in *Remington's Pharmaceutical Sciences*, 16th Ed., Mack Publishing Co., Easton, Pa. (1980).

Thus, as used herein, "polynucleotide" includes any functional derivative, fragments, variants, analogs, and chemical derivatives which may be substantially similar to the polynucleotides described herein and which possess similar activity.

DNA sequences for use in producing therapeutic and/or immunogenic peptides of the invention can also be obtained by several methods. For example, the DNA can be isolated using hybridization procedures which are well known in the art. These include, but are not limited to: 1) hybridization of probes to genomic or cDNA libraries to detect shared nucleotide sequences; 2) antibody screening of expression libraries to detect shared structural features and 3) synthesis by the polymerase chain reaction (PCR). The development of specific DNA sequences encoding or fragments thereof, can also be obtained by: 1) isolation of double-stranded DNA sequences from the genomic DNA: 2) chemical manufacture of a DNA sequence to provide the necessary codons for the polypeptide of interest; and 3) in vitro synthesis of a double-stranded DNA sequence by reverse transcription of mRNA isolated from a eukaryotic donor cell. In the latter case, a double-stranded DNA complement of mRNA is eventually formed which is generally referred to as cDNA.

Hybridization procedures are useful for the screening of recombinant clones by using labeled mixed synthetic oligonucleotide probes where each probe is potentially the complete complement of a specific DNA sequence in the hybridization sample which includes a heterogeneous mixture of denatured double-stranded DNA. For such screening, hybridization is preferably performed on either single-stranded DNA or denatured double-stranded DNA. Hybridization is particularly useful in the detection of cDNA clones derived from sources where an extremely low amount of mRNA sequences relating to the polypeptide of interest are present. In other words, by using stringent hybridization conditions directed to avoid non-specific binding, it is possible, for example, to allow the autoradiographic visualization of a specific cDNA clone by the hybridization of the target DNA to that single probe in the mixture.

A cDNA library believed to contain a polynucleotide of interest can be screened by injecting various mRNA derived from cDNAs into oocytes, allowing sufficient time for expression of the cDNA gene products to occur, and testing for the presence of the desired cDNA expression product, for example, by using antibody specific for a peptide encoded by the polynucleotide of interest or by using probes for the repeat motifs and a tissue expression pattern characteristic of a peptide encoded by the polynucelotide of interest. Alternatively, a cDNA library can be screened indirectly for expression of therapeutic and/or immunogenic peptides having at least one epitope using antibodies specific for the peptides. Such antibodies can be either polyclonally or monoclonally derived and used to detect expression product indicative of the presence of cDNA of interest.

Screening procedures which rely on nucleic acid hybridization make it possible to isolate any gene sequence from any organism, provided the appropriate probe is available. Oligonucleotde probes, which correspond to a part of the sequence encoding the protein in question, can be synthesized chemically. This requires that short, oligopeptide stretches of amino acid sequence must be known. The DNA sequence encoding the protein can be deduced from the genetic code, however, the degeneracy of the code must be taken into account. It is possible to perform a mixed addition reaction when the sequence is degenerate. This includes a heterogeneous mixture of denatured double-stranded DNA. For such screening, hybridization is preferably performed on either single-stranded DNA or denatured double-stranded DNA.

The naked polynudeotides may be conjugated to or used in association with other polynucleotides which operatively code for regulatory proteins that control the expression of these polypeptides or may contain recognition, promoter and secretion sequences. Those of ordinary skill in the art will be able to select regulatory polynucleotides and incorporate them into the naked polynucleotides of the invention (if not already present therein) without undue experimentation. For example, suitable promoters for use in murine or human systems and their use are described in *Current Protocols in Molecular Biology*, supra at Ch. 1.

A particularly preferred form of a naked polynucleotide for use in the invention will be one which has been incorporated into a plasmid vector. Use of a plasmid vector, particularly one which comprises a replicator, will prolong expression of the gene in target tissues. Certain plasmid vectors are also good mediators of immune responses to immunogenic peptides because high levels of expression are achieved when the gene encoding the peptides is incorporated into the vector.

Suitable plasmid vectors are well-known in the art and include the vectors described in *Current Protocols in Molecular Biology*, supra at Ch. 1. Two particularly preferred plasmid vectors are the pRSV (Rous sarcoma virus) and pCMV (cytomegalovirus) promoter vectors. Of these promoters, CMV is preferred for polynucleotides to be introduced into tissue other than muscle. This preference is based on observations that higher levels of expression are achieved in this context when the CMV promoter is employed.

A suitable protocol for isolation of the RSV promotor and its use in construction of a plasmid vector is described in Gorman, et al., *Proc. Natl. Acad. Sci, USA*, 79:6777, (1982). Other preferred plasmid vectors are pREP7 and pREV which are commercially available from Invitrogen of San Diego, Calif. For cloning of polynucleotides, a particularly suitable plasmid for production of mRNA is the pSP64T cloning vector described by Kreig, et al., *Nucleic Acids Res.*, 12:7057–7070, (1984). Any cDNA containing an initiation codon can be introduced into this plasmid and mRNA prepared from the expressed DNA templates using conventional techniques.

Various viral vectors that can be utilzed in the invention include adenovirus, herpes virus, vaccinia, or, preferably, an RNA virus such as a retrovirus. Preferably, the retroviral vector is a derivative of a murine or avian retrovirus. Examples of retroviral vectors in which a single foreign gene can be inserted include, but are not limited to: Moloney murine leukemia virus (MoMuLV), Harvey murine sarcoma virus (HaMuSV), murine mammary tumor virus (MuMTV), and Rous Sarcoma Virus (RSV). A number of additional retroviral vectors can incorporate multiple genes. All of these vectors can transfer or incorporate a gene for a selectable marker so that transduced cells can be identified and generated.

By inserting one or more sequences of interest into the viral vector, along with another gene which encodes the ligand for a receptor on a specific target cell, for example, the vector is now target specific. Retroviral vectors can be made target specific by inserting, for example, a polynucleotide encoding a sugar, a glycolipid, or a protein. Preferred targeting is accomplished by using an antibody to target the retroviral vector. Those of skill in the art will know of, or can readily ascertain without undue experimentation, specific polynucleotide sequences which can be inserted into the retroviral genome to allow target specific delivery of the retroviral vector containing the polynucleotides of interest. A separate vector can be utilized for targeted delivery of a replacement gene to the cell(s), if needed. In antisense therapy, an antisense oligonucleotide and the replacement gene may also be delivered via the same vector since the antisense oligonucleotide is specific only for target gene containing a polymorphism.

Since recombinant retoviruses are defective, they require assistance in order to produce infectious vector particles. This assistance can be provided, for example, by using helper cell lines that contain plasmids encoding all of the structural genes of the retrovirus under the control of regulatory sequences within the LTR. These plasmids are missing a nucleotide sequence that enables the packaging mechanism to recognize an RNA transcript for encapsidation. Helper cell lines that have deletions of the packaging signal include, but are not limited to, Ψ2, PA317 and PA12, for example. These cell lines produce empty virions, since no genome is packaged. If a retroviral vector is introduced into such helper cells in which the packaging signal is intact, but the structural genes are replaced by other genes of interest, the vector can be packaged and vector virion can be produced.

For purposes of monitoring expression, these vectors may be modified to include known reporter genes. For example, the pRSV lac-Z DNA vector described in Norton, et al., *Mol. Cell. Biol.*, 5:281, (1985), may produce β-galactosidase with protein expression. Luciferase and chloramphenicol acetyl transferase ("CAT"; see, e.g., Gorman, et al., supra, re construction of a pRSV-CAT plasmid) may also be used. Convenient plasmid propogation may be obtained in *E. coli* (see, e.g., *Molecular Cloning: A Laboratory Manual*, supra.)

For use as a tolerizing vaccine, a mixture of polynucleotides or separately coadministered group of polynucleotides may include a gene operatively encoding for an immunosuppressive cytokine (such as TGFβ) and a separate gene operatively encoding for a relevant histocompatibility protein. This approach could be adapted for use in inducing tolerance to foreign antigens (including alloantigens) as well as self-antigens.

For use in antisense therapy, synthetic antisense oligonucleotides are generally between 15 and 25 bases in length. Assuming random organization of the human genome, statistics suggest that a 17-mer defines a unique sequence in the cellular mRNA in human DNA; a 15-mer defines a unique sequence in the cellular mRNA component. Thus, substantial specificity for a selected genetic target is easily obtained using the synthetic oligomers of this invention.

In the cell, the antisense nucleic acids hybridize to the corresponding mRNA, forming a double-stranded molecule. The antisense nucleic acids, interfere with the translation of the mRNA, since the cell will not translate a mRNA that is double-stranded. Antisense oligomers of about 15 nucleotides are preferred, since they are easily synthesized and are less likely to cause problems than larger molecules when introduced into the target nucleotide mutant producing cell. The use of antsense methods to inhibit the in vitro translation of genes is well known in the art (Marcus-Sakura, *Anal.Biochem.*, 172:289, 1988). Less commonly, antisense molecules which bind directly to the DNA may also be used.

Ribozymes are RNA molecules possessing the ability to specifically cleave other single-stranded RNA in a manner analogous to DNA restriction endonucleases. Through the modification of nucleotide sequences that encode these RNAs, it is possible to engineer molecules that recognize specific nucleotide sequences associated with production of a mutated proto oncogene or tumor suppressor gene in an RNA molecule and cleave it (Cech, *J.Amer.Med. Assn.*, 260:3030, 1988). A major advantage of this approach is that, because they are sequence-specific, only target mRNAs with particular mutant sequences are inactivated.

There are two basic types of ribozymes, namely, tetrahymena-type (Hasselhoff, *Nature*, 334:585, 1988) and "hammerhead"-type. Tetrahymena-type ribozymes recognize sequences which are four bases in length, while "hammerhead"-type ribozymes recognize base sequences 11–18 bases in length. The longer the recognition sequence, the greater the likelihood that the sequence will occur exclusively in the target mRNA species. Consequently, hammerhead-type ribozymes are preferable to tetrahymena-type ribozymes for inactivating a specific mRNA species, and 18-based recognition sequences are preferable to shorter recognition sequences.

Unmodified oligodeoxyribonucleotides are readily degraded by serum and cellular nucleases. Therefore, as is well known in the art, certain modifications of the phosphate backbone have conferred nuclease resistance to antisense DNA. For instance phosphorothioate, methylphosphonate, and α-anomeric sugar-phosphate, backbone-modified oligomers have increased resistance to serum and cellular nucleases. In addition, methylphosphonates are nonionic and offer increased lipophilicity to improve uptake through cellular membranes. The use of modified oligonucleotides as antisense agents may require slightly longer or shorter sequences because chemical changes in molecular structure can affect hybridization (L. A. Chrisey et al., *BioPharm*, 4:36–42, 1991). These backbone-modified oligos bind to a target sequence and exert their inhibitory effects by blocking the binding of the cell's translational machinery to a specific RNA or by inducing ribonuclease H activity through the formation of RNA/DNA duplex structures.

B. Pharmaceutical Preparations of Naked Polynucleotides

Compositions of naked polynucleotides and mixtures of polynucleotides may be placed into a pharmaceutically acceptable suspension, solution or emulsion. Suitable mediums include saline and may, for those embodiments which do not rely on antigen presenting cells for delivery of the polynucleotides into target tissue, liposomal preparations.

More specifically, pharmaceutically acceptable carriers may include sterile aqueous of non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils. Intravenous vehicles include fluid and nutrient replenishers, electrolyte replenishers (such as those based on Ringer's dextrose), and the like. Preservatives and other additives may also be present such as, for example, antimicrobials, antioxidants, chelating agents, and inert gases and the like. Further, a composition of naked polynucleotides may be lyophilized using means well known in the art, for subsequent reconstitution and use according to the invention.

For those embodiments of the invention which do not rely on APC recognition of naked polynucleotides as antigen, in addition to the targeted vector delivery systems discussed supra, a colloidal dispersion system may also be used for targeted delivery. However, it will be appreciated by those of skill in the art that the advantages of employing the method of the invention to administer naked nucleotides, and of administering those nucleotides to tissues having relatively high concentrations of antigen presenting cells, are such that the use of collodidal dispersion systems for delivery of polynucleotides will not be a preferred method. The discussion below regarding such systems is therefore provided principally for reference in the event that the preferred method of the invention is determined to be unavailable for use with respect to a particular indication.

Colloidal dispersion systems include macromolecule complexes, nanocapsules, microspheres, beads, and lipid-based systems including oil-in-water emulsions, micelles, mixed micelles, and liposomes. The preferred colloidal system of this invention is a liposome.

Liposomes are artificial membrane vesicles which are useful as delivery vehicles in vitro and in vivo. It has been shown that large unilamellar vesicles (LUV), which range in size from 02–4.0 μm can encapsulate a substantial percentage of an aqueous buffer containing large macromolecules. RNA, DNA and intact virions can be encapsulated within the aqueous interior and be delivered to cells in a biologically active form (Fraley, et al., *Trends Biochem. Sci.*, 6:77, 1981). In addition to mammalian cells, liposomes have been used for delivery of polynucleotides in plant, yeast and bacterial cells. In order for a liposome to be an efficient gene transfer vehicle, the following characteristics should be present: (1) encapsulation of the genes encoding the antisense polynucleotides at high efficiency while not compromising their biological activity; (2) preferential and substantial binding to a target cell in comparison to non-target cells; (3) delivery of the aqueous contents of the vesicle to the target cell cytoplasm at high efficiency; and (4) accurate and effective expression of genetic information (Mannino, et al., *Biotechniques*, 6:682, 1988).

The composition of the liposome is usually a combination of phospholipids, particularly high-phase-transiton-temperature phospholipids, usually in combination with steroids, especially cholesterol. Other phospholipids or other lipids may also be used. The physical characteristics of liposomes depend on pH, ionic strength, and the presence of divalent cations.

Examples of lipids useful in liposome production include phosphatidyl compounds, such as phosphatidylglycerol, phosphatidylcholine, phosphatidylserine, phosphatidylethanolamine, sphingolipids, cerebrosides, and gangliosides.

Particularly useful are diacylphosphatidylglycerols, where the lipid moiety contains from 14–18 carbon atoms, particularly from 16–18 carbon atoms, and is saturated. Illustrative phospholipids include egg phosphatidylcholine, dipalmitoylphosphatidylcholine and distearoylphosphatidylcholine.

The targeting of liposomes can be classified based on anatomical and mechanistic factors. Anatomical classification is based on the level of selectivity, for example, organ-specific, cell-specific, and organelle-specific. Mechanistic targeting can be distinguished based upon whether it is passive or active. Passive targeting utilizes the natural tendency of liposomes to distribute to cells of the reticuloendothelial system (RES) in organs which contain sinusoidal capillaries. Active targeting, on the other hand, involves alteration of the liposome by coupling the liposome to a specific ligand such as a monoclonal antibody, sugar, glycolipid, or protein, or by changing the composition or size of the liposome in order to achieve targeting to organs and cell types other than the naturally occurring sites of localization.

The surface of the targeted delivery system may be modified in a variety of ways. In the case of a liposomal targeted delivery system, lipid groups can be incorporated into the lipid bilayer of the liposome in order to maintain the targeting ligand in stable association with the liposomal bilayer. Various linking groups can be used for joining the lipid chains to the targeting ligand.

For those embodiments of the invention which do rely on APC expression, liposomal preparations substantially limit uptake of the naked polynucleotides in vivo and should not be used. Instead, isotonic buffered soluton is the preferred medium for maximal uptake of the naked polynucleotides in such embodiments. Further, use of absorption promoters, detergents, chemical irritants or mechanical irtitation means is also preferred to enhance transmission of the naked polynucleotide composition through the point of entry. For reference concerning general principles regarding promoters and detergents which have been used with success in mucosal delivery of organic and peptide-based drugs, see Chien, *Novel Drug Delivery Systems*, Ch. 4 (Marcel Dekker, 1992). Specific information concerning known means and principles of nasal drug delivery are discussed in Chien, supra at Ch 5. Examples of suitable nasal absorption promoters are set forth at Ch. 5, Tables 2 and 3; milder agents are preferred. Further, known means and principles of transdermal drug delivery are also discussed in Chien, supra, at Ch. 7. Suitable agents for use in the method of this invention for mucosal/nasal delivery are also described in Chang, et al., *Nasal Drug Delivery*, "Treatise on Controlled Drug Delivery", Ch. 9 and Table 3–4B thereof, (Marcel Dekker, 1992). Suitable agents which are known to enhance absorption of drugs through skin are described in Sloan, *Use of Solubility Parameters from Regular Solution Theory to Describe Partitioning-Driven Processes*, Ch. 5, "Prodrugs: Topical and Ocular Drug Delivery" (Marcel Dekker, 1992), and at places elsewhere in the text.

It is expected that these techniques (and others which are conventionally used to facilitate drug delivery) may be adapted to preparation of naked polynucleotides for use in the methods of the invention by those of ordinary skill in the art without undue experimentation. In particular, although the approaches discussed in the preceding paragraphs have not, to the inventors' knowledge, been previously used for polynucleotide delivery, it is believed that they are suitable for use to that end. For that reason, the references identified above, while not essential to the inventive methods, are incorporated herein by this reference. Specific examples illustrating this suitability are set forth infra.

C. Means For, And Routes Of, Administration of Naked Polynucleotides.

For dermal routes of administration, the means of introduction may be by epidermal administration, subcutaneous or intradermal injection. Of these means, epidermal administration is preferred for the greater concentrations of APC's expected to be in intradermal tissue.

The means of introduction for dermal routes of administration which are most preferred, however, are those which are least invasive. Preferred among these means are transdermal transmission and epidermal administration.

For transdermal transmission, iontophoresis is a suitable method. Iontophoretic transmission may be accomplished using commercially available "patches" which deliver their product continuously through unbroken skin for periods of several days or more. Use of this method allows for controlled transmission of pharmaceutical compositions in relatively great concentrations, permits infusion of combination drugs and allows for contemporaneous use of an absorption promoter.

An exemplary patch product for use in this method is the LECTRO PATCH trademarked product of General Medical Company of Los Angeles, Calif. This product electronically maintains reservoir electrodes at neutral pH and can be adapted to provide dosages of differing concentrations, to dose continuously and/or to dose periodically. Preparation and use of the patch should be performed according to the manufacturer's printed instructions which accompany the LECTRO PATCH product; those instructions are incorporated herein by this reference.

Epidermal administration essentially involves mechanically or chemically irritating the outermost layer of the epidermis sufficiently to provoke an immune response to the irritant. Specifically, the irritation should be sufficient to attract APC's to the site of irritation. As discussed previously, it is believed that the APC's then take up and express the administered naked polynucleotide.

An exemplary mechanical irritant means employs a multiplicity of very narrow diameter, short tynes which can be used to irritate the skin and attract APC's to the site of irritation, to take up naked polynucleotides transferred from the end of the tynes. For example, the MONO-VACC old tuberculin test manufactured by Pastuer Merieux of Lyon, France contains a device suitable for introduction of naked polynucleotides.

The device (which is distributed in the U.S. by Connaught Laboratories, Inc. of Swiftwater, Pa.) consists of a plastic container having a syringe plunger at one end and a tyne disk at the other. The tyne disk supports a multiplicity of narrow diameter tynes of a length which will just scratch the outermost layer of epidermal cells. Each of the tynes in the MONO-VACC kit is coated with old tuberculin; in the present invention, each needle is coated with a pharmaceutical composition of naked polynucleotide or a mixture thereof. Use of the device is according to the manufacturer's written instructions included with the device product; these instructions regarding use and administration are incorporated herein by this reference to illustrate conventional use of the device. Similar devices which may also be used in this embodiment are those which are currently used to perform allergy tests.

Another suitable approach to epidermal administration of naked polynucleotides is by use of a chemical which irritates the outermost cells of the epidermis, thus provoking a sufficient immune response to attract APC's to the area. An example is a keratinolytic agent, such as the salicylic acid used in the commercially available topical depilatory creme sold by Noxema Corporation under the trademark NAIR. This approach may also be used to achieve epithelial administration in the mucosa. The chemical irritant may also be applied in conjunction with the mechanical irritant (as, for example, would occur if the MONO-VACC type tyne were also coated with the chemical irritant). The naked polynucleotide may be suspended in a carrier which also contains the chemical irritant or coadministered therewith.

For mucosal administration, the means of introduction will vary according to the location of the point of entry. Particularly for immunization to and treatment of respiratory infections, intranasal administration means are most preferred. These means include inhalation of aerosol suspensions or insufflation of the naked polynucleotide or mixtures thereof. Suppositories and topical preparations will also be suitable for introduction to certain mucosa, such as genital and ocular sites. Also of particular interest with respect to vaginal delivery of naked polynucleotides are vaginal sandwich-type rings and pessaries. Examples of these devices and their use are described in Chien, supra at Ch.9.

The dosage of each naked polynucleotide or mixture thereof to be supplied using the method of the invention will vary depending on the desired response by the host and the polynucleotide used. Generally, it is expected that up to 100–200 $\mu$g of DNA can be administered in a single dosage, although as little as about 0.3 $\mu$g of DNA administered through skin or mucosa can induce long lasting immune responses.

For purposes of the invention, however, it is sufficient that the naked polynucleotides be supplied at a dosage sufficient to cause expression of the biologically active peptide encoded by the polynucleotide. Dosages suitable for particular indications (e.g., supplying a subtherapeutic dosage of cytokine) are illustrated by the discussion and examples provided below.

These dosages may be modified to achieve therapeutic, subtherapeutic or immunogenic levels of expression. Means to confirm the presence and quantity of expressed peptides are well-known to those skilled in the art and will not, therefore, be described in detail. Certain such means are illustrated in the Examples provided below; generally, they include immunoassays (such as enzyme-linked immunosorbent assays), PCR techniques, and immunohistological analyses performed according to techniques which are well known in the art. Dosages of the administered polynucleotides can be adjusted to achieve the desired level of expression based on information provided by these detection and quantification means as well as in vivo clinical signs known to practitioners skilled in the clinical arts.

II. Introduction of Naked Polynucleotides to Express Subtherapeutic Levels of Cytokines and Other Proteins Important in the Incidence of Age-Associated Illnesses The methods described above for preparation and introduction of naked polynucleotides are suitable for use in this embodiment of the invention. In this embodiment, the methods described are employed to produce subtherapeutic levels of circulating cytokines and related proteins. As noted above, the quantity of naked polynucleotide necessary to produce subtherapeutic levels of expressed protein can be readily determined and adjusted as necessary by skilled clinicians.

This aspect of the invention is practiced by administering a polynucleotide or recombinant mixture thereof to a mammal which operatively encodes for the desired protein, preferably prior to the onset of biological impairment associated with aging. For example, for patients at high risk for developing an illness associated with a compromised immune system, subtherapeutic levels of an immunostimulatory interleukin (such as IL-2) would be administered so as to generate a continuous level of protein expression prior to the onset of disease as determined, for example, by observance of the surrogate end point for the disease. For patients at high risk of disease, the therapy may be continued throughout the patient's life span. To allow the patient to accommodate this prolonged course of therapy, individual doses of polynudeotide (and resulting levels of protein expression) must be low (i.e., subtherapeutic). However, the polynucleotides can be expected to degenerate far more slowly than would the protein (i.e., a difference of months) so the doses may be administered less frequently, thus minimizing the risk of toxicity and trauma to the patient.

More specifically, administration of the desired polynucleotides will begin prior to or concurrent with onset of a disease state associated with aging or another biological event which results in the compromise of the immune system, such as the loss of CD4 T cells during the course of an HIV-1 infection. Prolonged, continuous therapy beginning prior to the onset of a disease state or loss of immune function is preferred. Therapy is accomplished by subtherapeutic levels of expression of the genes of interest, in particular of genes encoding for cytokines (e.g., interleukins and lymphotoxins).

Most preferably, at least one of the genes of interest will be those which encode for IL-1, IL-2, growth hormone (GH), somatomedins (such as insulin-like growth factor [IGF-1]), and/or TGFβ. These proteins control or can influence a magnitude of immune responses (e.g., IL-2, IL-1, GH and IGF-1), the systemic response to stress or injury (e.g., IL-1), tissue cellularity (GH and IGF-1) and the deposition of extracellular matrix proteins and connective tissue (TGFβ), the latter of which exerts greater biological effect as the activity of IL-1 and IL-2 declines.

It will be appreciated that this particular method of the invention is, in part, a subset of the method disclosed in Section I, supra. However, those of skill in the art will understand that it is possible for this embodiment of the invention to be practiced using polynucleotides that are not "naked"; i.e., polynucleotides that are conjoined to a colloidal dispersion system. Nonetheless, the advantages of the method disclosed in Section I, supra, are such that its practice (i.e., using "naked" polynucleotides introduced into a tissue having a relatively high proportion of APC's) will be much preferred.

III. Administration of Naked Polynucleotide Cocktails

Another aspect of the invention is the administration of a peptide cocktail (i.e., mixture of polynucleotides) via expression of gene constructs containing, for example, up to 200 polynucleotide sequences under the control of a single promoter. This embodiment will be of particular use in treating infections by agents of different species which cause similar symptoms. For example, there are over 100 known species of rhinoviruses which cause respiratory illnesses having similar clinical symptoms. Rather than undertaking the identification of the particular infecting species (a laborious and often inexact process), a cocktail vaccine could be administered according to the method of the invention which is capable of stimulating an immune response to many different rhinoviruses. This approach also allows for the construction of a vaccine to various strains of HIV, using pooled isolates of envelope genes from different patients (which genes may, if necessary, then be amplified).

Administration of mbiures of polynucleotides could also serve to deliver peptides having more than one biological activity. For example, a naked polynucleotde operatively encoding for an immunogenic peptide may be coupled to or administered with a naked polynucleotide operatively encoding an antbody in such a way that both peptde and antibody will be expressed.

To illustrate, administration of genes which will jointly express IL-2 and anti-gp71 may (based on results obtained with the IL-2 protein) result in localization of the antibody in tumor tissue developed in response to murine leukemia virus (MuLV) in mice (see, re results obtained with concurrent administration of IL-2/anti-gp71 mAb's, Schultz, et al., Cancer Res., 50:5421–5425, 1990).

Examples illustrating aspects of each embodiment of the invention are provided below. They should be regarded as illustrating rather than limiting the invention.

EXAMPLE I

LOCALISED DELAYED HYPERSENSITIVITY RESPONSES IN MICE OCCUR FOLLOWING INTRAMUSCULAR INJECTIONS OF NAKED POLYNUCELOTIDE

Although (consistent with previously reported results) intramuscular injection of naked plasmid cDNA results in expression of peptides encoded by the polynucleotides, it also (contrary to previously reported results) elicits an immune response to the gene in the muscle tissue. With co-injecton of 2 plasmids, this inflammatory response becomes chronic, with myonecrosis being exhibited. Both responses are consistent with a diagnosis of a localized delayed hypersensitivity response to the gene at its point of entry, i.e., muscle tissue. Contrary to previous assumptions, it is this inflammatory response rather than uptake by muscle cells which is likely (if not solely) responsible for expression of naked polynucleotides following intramuscular injections thereof.

To illustrate the immune response caused by intramuscular injection of naked cDNA, pREVk3 and pRSVIL2 were prepared as follows.

Preparation of Plasmids. A rearranged kappa light gene from a human patient with chronic lymphocytic leukemia was isolated which contains a Humkv 325 (which encodes the 17.109 cross-reactive idiotype commonly expressed by IgM autoantibodies and chronic lymphocytic leukemia cells). This gene is known in the art and is described, for example, in Martin, et al J. Exp. Med., 175:983, (1992), which article is incorporated herein by this reference.

A 1040 bp HindIII-XhoI fragment containing the V-J region of this gene was excised and inserted into the polycloning site of the mammalian expression vector pREP7 (Invitrogen, San Diego, Calif.), downstream of the Rous sarcoma virus (RSV) long terminal repeat (LTR) to produce a vector designated pREVk3. Downstream of the rearranged JK1 segment, there is a natural stop codon, which terminates translation.

To produce an IL-2 expression vector, designated pRSVIL-2, the luciferase cDNA in the vector pRSVL (Wolff, et al., Science, 247:1465, 1990) was replaced with a 680 bp HindIII-BamHI fragment of pBC12/HIV/IL-2 (American Type Culture Collection, No. 67618) according to the method taught in Cullen, Cell, 46:937, (1986). The Wolff, et al., and Cullen references are incorporated herein to illustrate knowledge in the art concerning construction of these expression vectors.

Intramuscular injection of mice with plasmid cDNA. Eight week old BALB/c mice were anesthetized with methoxyflurane. Plasmid cDNA (100 μg per injection) was suspended in 100 μl of saline, and then was injected four times into the quadricep muscles through a 28-gauge needle at weekly intervals. One group of six mice received 100 μg of pREVk3. Another group of six mice received 100 μg each of pREVk3 and pRSVIL-2 while a third group received 100 μg of saline alone. Just before every injection, blood samples were collected from the orbital arteries.

ELISA To Verify In Vivo Gene Expression by the Plasmids. Antibodies against Humkv325 products were measured by ELISA (enzyme-linked immunosorbent assay). The IgM rheumatoid factor Glo is encoded by the Humkv325 gene and has 17.109 idiotype positive kappa light chains. The purified protein was dissolved at 10 μg/ml in 0.1 M borate, 02 M NaCl, pH8.2 (i.e., buffered borate saline or BBS), and then 100 μl aliquots were added to the wells of plastic microtiter plates. After overnight incubation at 4° C., the plates were washed twice with BBS containing 0.5% Tween-20 (BBS/Tween), and were quenched with BBS supplemented with 1% bovine serum albumin (BBS/BSA) for four hours at room temperature. After washing twice with BBS/Tween, samples diluted serially in BBS/BSA were distributed to the wells in duplicate. After incubation for three hours at room temperature, the plates were washed four times with BBS/Tween, and then were incubated with biotinylated gout anti-mouse IgG (Kirkegaard & Perry, Gaithersburg, Md.) diluted to 1:2000 in BBS/BSA One hour later, the plates were washed four times with BBS/Tween, and incubated with 25 μl of TMB peroxidase substrate (Kirkegaard & Perry). Thirty minutes later absorption at 450 nm was measured in a microplate reader (Molecular Devices, Menlo Park, Calif.). To estimate the antibody content in the immune sera, the results were compared to a standard curve made with monoclonal antibody 17.109 (see, e.g., the description of this mAb at Carson, et al., (1983) *Mol. Immunol.* 20:1081–1087).

These assays showed that production of the antibodies of interest had been enhanced, thereby confirming expression of the genes by the plasmids.

Histological evaluation. At day 49 the intramuscularly injected mice were sacrificed. Muscles into which the genes had been injected were fixed in 10% formalin and processed for histological evaluation.

Figure 1C:
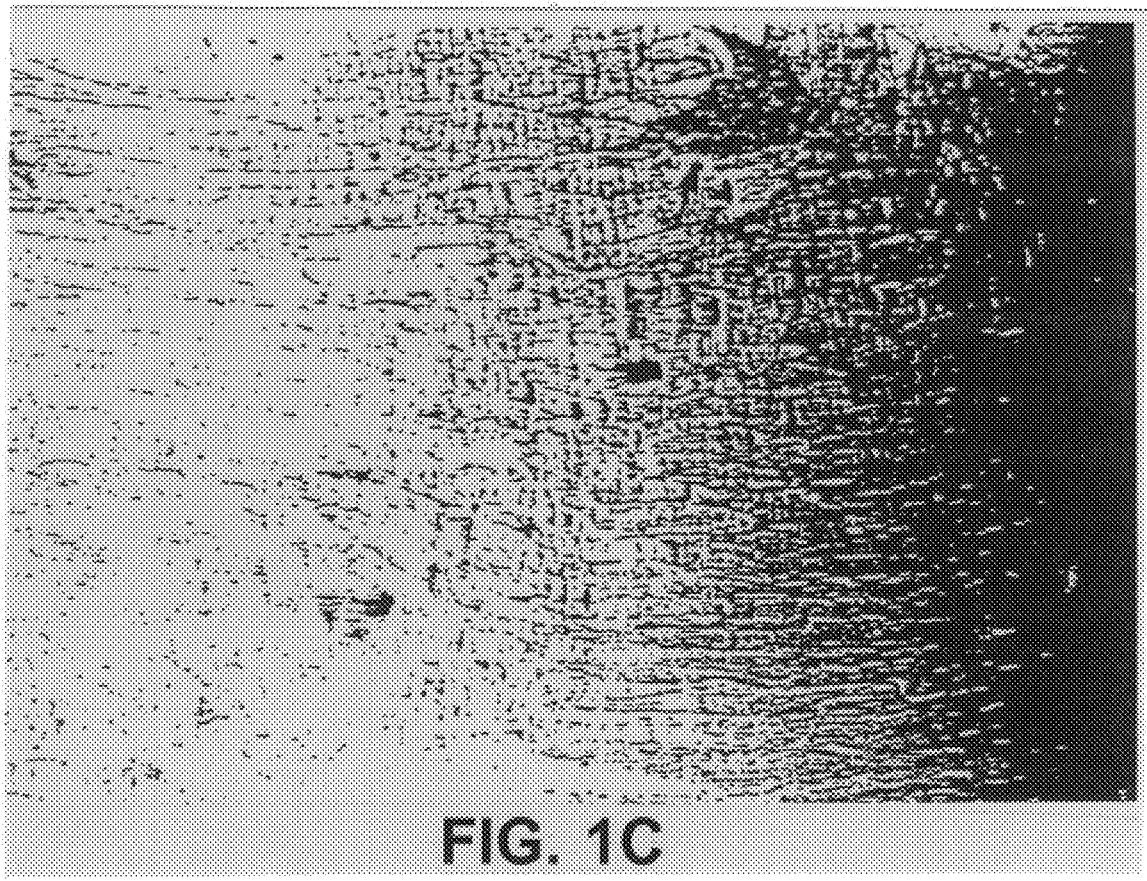

Sections from muscles that had been coinjected with pREVk3 and pRSVIL2, demonstrated chronic inflammation and myonecrosis, consistent with a localized delayed hypersensitivity response (FIGS. 1A and B). In contrast, muscles injected with pREVk3 or pRSVIL2 alone had a lymphoid infiltrate localized to the site of subcutaneous injection (FIG. 1C).

EXAMPLE II

GENE EXPRESSION FOLLOWING INTRADERMAL INJECTION OF A NAKED POLYNUCLEOTIDE

To explore alternatives to intramuscular injections of naked polynucleotides, mice were injected with a naked cDNA plasmid intradermally. Gene expression was observed and measured.

The gene for influenza ribonucleoprotein (RNP) was subcloned into a pCMV plasmid as described above. RNP genes from numerous strains of influenza are known in the art and are highly conserved in sequence among various strains (see, e.g. Gorman, et al., *J. Virol*, 65:3704, 1991).

Four eight week old Balb/c mice were injected three times with 15 μg of pCMV-RNP suspended in 100 μl of HBSS. Injections were made intradermally at the base of the tails at two week intervals. Cytotoxic T lymphocytes (CTL) recognize antigens presented by class I MHC molecules and play an important role in the elimination of virally infected cells. Intramuscular (i.m.) immunization by means of cDNA expression vectors should be an effective method to introduce antigen into class I MHC molecules and thus stimulate CTL responses. In this study, intradermal (i.d.) injection of a plasmid containing the influenza nucleoprotein (NP) antigen gene induced both NP-specific CTL and high titers of anti-NP antibodies. These antibodies reached a maximum 6 weeks after injection and persisted unchanged for at least 28 weeks, in the absence of local inflammation.

Plasmid DNA was purified by CsCl banding in the presence of ethidium bromide and was stored frozen in 10 mM Tris-HCL, 0.1 mM EDTA, pH 8.0. Before injection, the plasmid was precipitated in ethanol and dissolved in normal saline containing 0.1 mM EDTA.

Figure 2A:
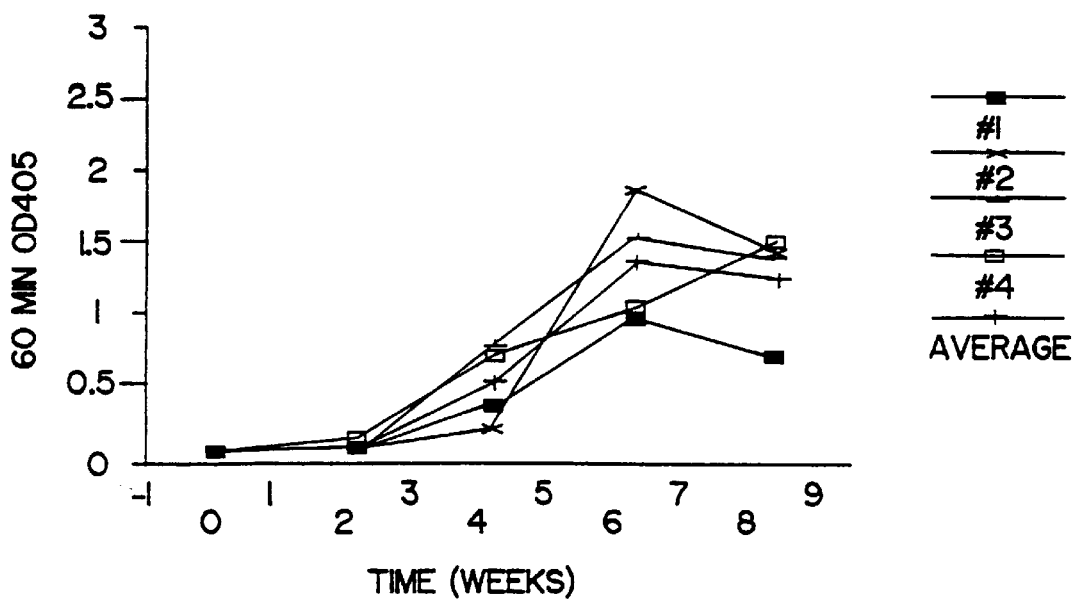
FIGS. 2A and 2B depict the results of an ELISA for anti-NP IgG in serum following intradermal injection of naked pCMVRNP.
Figure 2B:
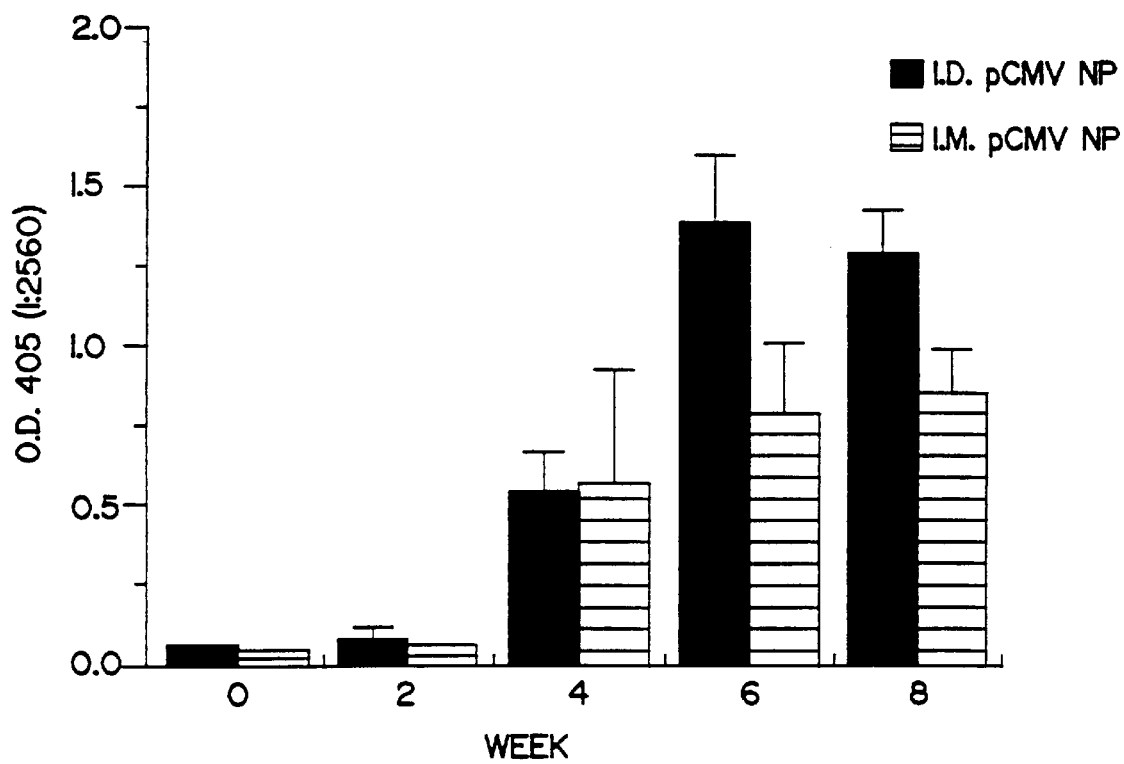

The presence of anti-NP IgG in serum was measured by ELISA substantially as described in Viera, et al., *Int. Immunl.*, 2:487, (1990). The results of this assay are shown in FIG. 2A; all of the animals developed high titer anti-NP antibodies, which persisted for more than 20 weeks. As shown in FIG. 2B, the intradermal injections appeared to give about four fold higher antibody titers than intramuscular injections (made as described in Example I) of equivalent amounts of plasmid DNA.

The axes of FIG. 2 represent, respectively, the ELISA titer (mean, 1 ounce) against time. Serum dilution for all graph points is 2560.

EXAMPLE III

GENE EXPRESSION FOLLOWING INTRANASAL INTRODUCTION OF A NAKED POLYNUCLEOTIDE

Using the same plasmid (pCMV-RNP) in the same HBSS suspension described in Example II, naked polynucleotide encoding for influenza ribonucleoprotein was introduced to Balb/c mice in 3 groups of 6 intranasally. Levels of anti-NP IgG in peripheral blood before and after introduction of the plasmid at various serum dilutions were measured by ELISA as described in Example II. Blood was drawn from each mouse after intranasal introduction after 6 weeks.

Figure 3:
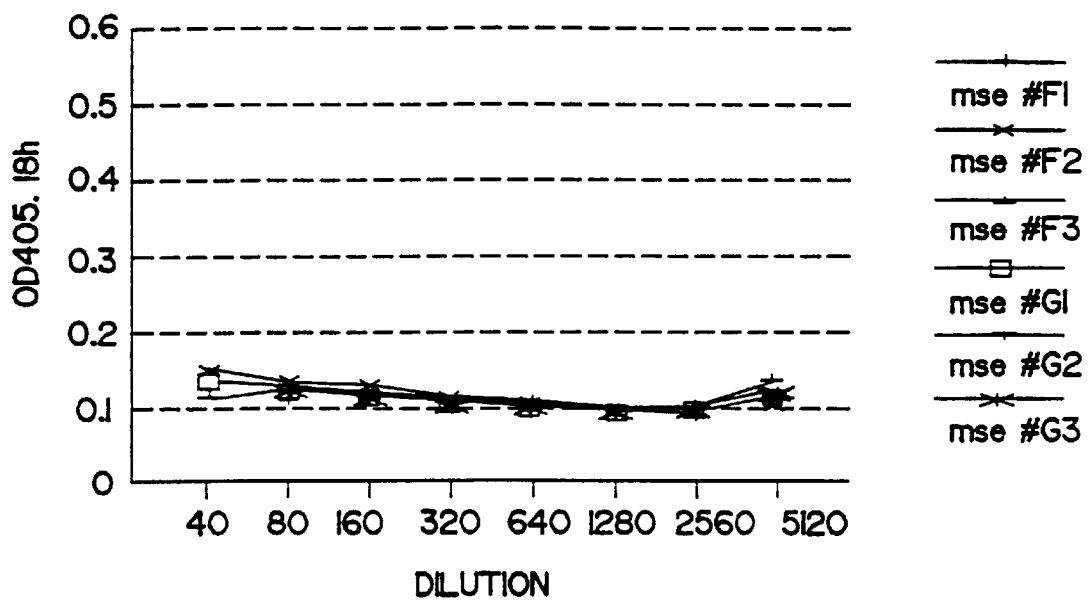
FIG. 3 depicts the results of an ELISA for anti-NP IgG before intranasal introduction of naked pCMVRNP to Balb/c mice.

FIG. 3 graphically depicts the results of the ELISA assays before and after intranasal introduction of the plasmid. The graphs plot ELISA titer against serum dilution. In FIG. 3, values are shown for individual mice from each group (#1–3) and an average value from all mice in each group (#G1–G3).

Figure 4:
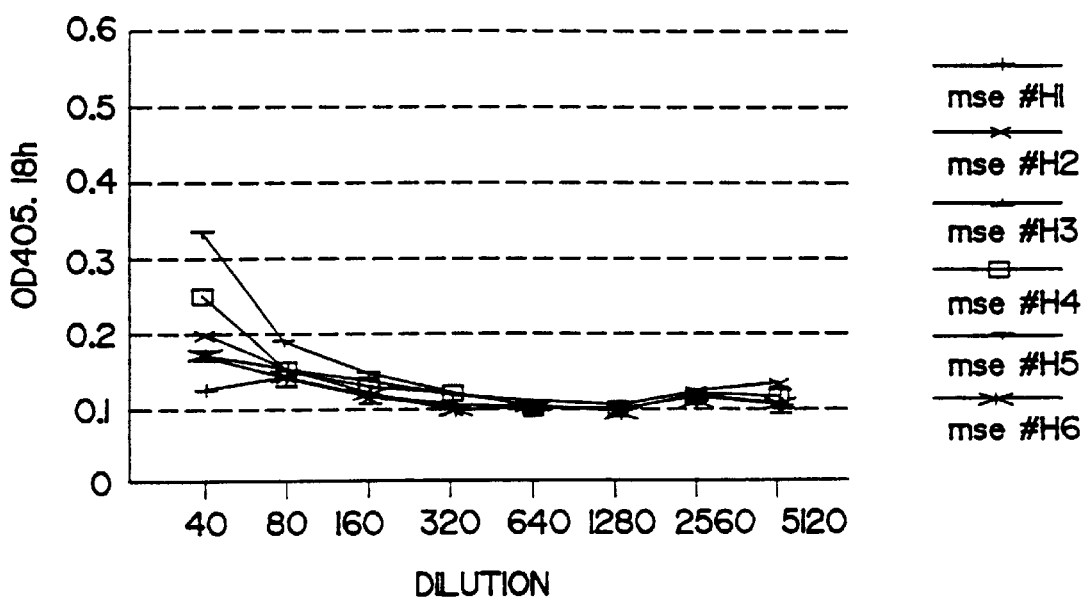
FIG. 4 depicts the results of an ELISA for ant-NP IgG in an unanesthesized group of Balb/c mice.

Without anesthesia, mice in a second group which received 3×7.5 μg of plasmid showed enhanced titers of antibody as compared to background (FIG. 3). These data are shown in FIG. 4.

Figure 5:
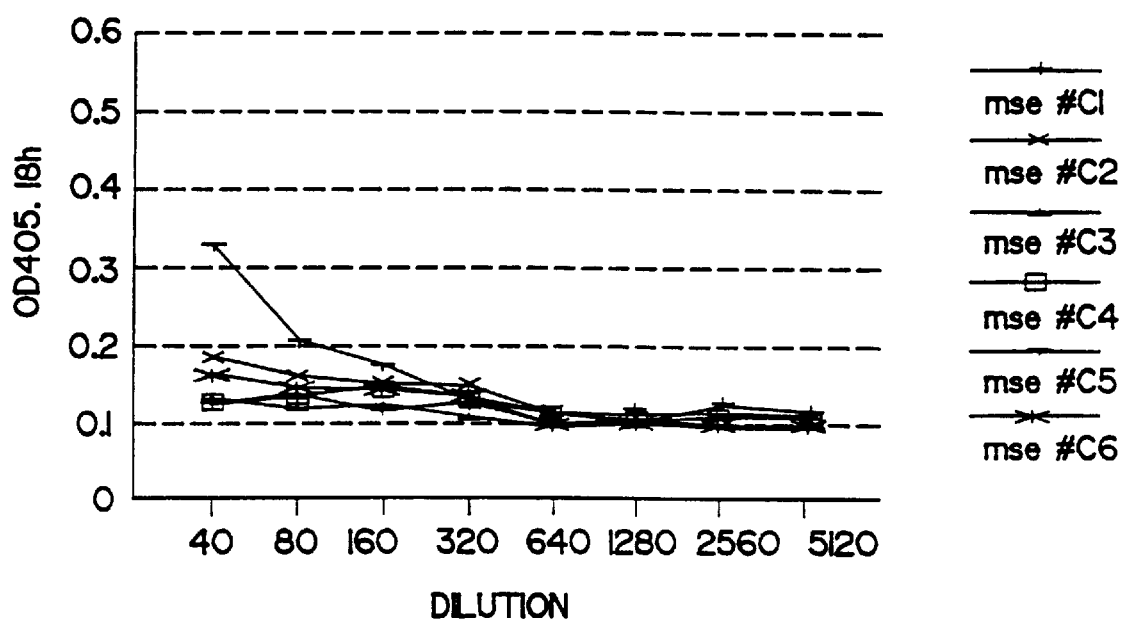
FIG. 5 depicts the results of an ELISA for anti-NP IgG in an anesthesized group of Balb/c mice.

A third group of mice received the same gravity of plasmid under anesthesia. Expression of RNP as indicated by titers of anti-NP IgG in these mice was substantially similar to the expression achieved in the unanethesized mice. The data for the anethesized mice are shown in FIG. 5.

Expression can be enhanced by additional use of absorption promoters, and prolonged by time-released promoters whose identity and use are known in the art such as those suggested in Chien, supra, at Ch. 5.

EXAMPLE IV

EXPRESSION OF SUBTHERAPEUTIC LEVELS OF CYTOKINES AND SYSTEMIC RESPONSES THERETO FOLLOWING ADMINISTRATION OF NAKED IL-2, TGF-β1 AND IL-4 GENES

Construction of Expression Vectors for IL-2, TGF-β1, and IL-4. The cDNAs for human (h) IL-2 (ATCC 67618), TGF-β1 (ATCC 59954), and mouse IL4 (ATCC 37561) were subcloned into the vector pBSII SK (from Invitrogen, San Diego, Calif.) to generate 5'-HindIII and 3'-Sma1 sites. These were used to replace the HindIII-BamH1 luciferase cDNA fragment in the expression vector pRSVL described in Example I. The resulting expression vectors (pRSVIL2, pRSVTGFβ1, and pRSVIL4) contain the Rous Sarcoma Virus (RSV) long terminal repeat (LTR) promoter, and an SV40 polyadenylation site. Plasmid DNA was purified from transformed DH5α *E coli* using QIAGEN kits from Qiagen, of Chatsworth, Calif.

The activities of the three vectors were confirmed by transient lipofection of mouse $C_2C_{12}$ myoblasts (ATCC [American Type Culture Collection, Rockford, Md.] CRL 1772), as described in Lotz, et al., *J. Exp. Med.*, 167:1253, (1988) which is incorporated herein by this reference. In each case, supernatants obtained 48 hours after lipofection contained biologically active cytokine, as determined by the lymphocyte activation factor (LAF) assay, using murine C3H/HeF thymocytes, in the presence or absence of the appropriate specific neutralizing antibodies (R&D Systems, Minneapolis, Minn.).

Experimental Design. Five-week old Balb/c mice were purchased from Jackson Laboratory (Bar Harbor, Me.). At 6 weeks of age (day 0) animals were divided into 4 groups of four mice. At days 0, 7 and 14, groups 2–4 were injected with a 28-gauge needle intramuscularly (i.m.) at 5 different sites in the right thigh with a total of 100 μg of plasmid DNA (pRSVIL2, pRSVTGFβ1 or pRSVIL4) dissolved in 100 μl of normal saline. At days 3, 10, and 17 (3 days after the cytokine gene injections) all animals were immunized with 100 μg of keyhole limpet hemocyanin (KLH) (Sigma, St Louis, Mo.), dispersed in 100 μl of IMJECT ALUM (aluminum hydroxide, Pierce, Rockford, Ill.) intramuscularly in the same thigh.

The second set of experiments followed a similar protocol. Five groups of eight mice each were injected in the right thigh with 100 μg of plasmid DNA (PRSVIL2, pRSVTGFβ1 or pRSVIL4, groups 2–4 respectively). Group 1 was injected with normal saline, while group 5 was injected with 100 μg of pRSVIL2 and 100 μg of pRSVTGFβ.

In contrast to the first experiments, the antigen (human transferrin (Sigma)) was injected under the same condifions, intramuscularly in the left shoulder. At day 56 or 63, mice were boosted subcutaneously with 50 μg of antigen (KLH or transferrin, respectively) suspended in 50 μl normal saline. All animals were bled weekly from the retroorbital plexus for measurement of antibody levels.

Six-week-old MRL/lpr/lpr mice (Jackson Laboratory; 10 mice/group) were injected three times at four-week intervals following the same method with 100 μg of pRSVIL2, pRSVTGFβ1 or pRSVnull (i.e., no introduced gene). Mice were bled at 16 weeks, two weeks after the last injection for measurement of antichromatin antibody levels. In the transferrin experiment, three mice from the pRSVTGFβ1 group, one mouse from the control group, and one mouse from the pRSVIL2 groups, died during bleeding or anesthesia.

Antibody Assays to Confirm the Effect on Antigen Response Caused by Expression of Cytokines by the cDNA Plasmids. Wells of microtiter plates (Costar #3590, Cambridge, Mass.) were coated with human transferrin (100 μl/well, 10 μg/ml in borate buffered saline (BBS) pH 8.0 overnight), and washed with the same buffer and quenched with a 19% bovine serum albumin (BSA) solution in BBS. After washing twice in BBS 0.5% Tween 20, serum samples diluted 1:1000 in phosphate buffered saline pH 7.4 (PBS) were added to duplicate wells. After overnight incubation at 4° C., the plates were washed with BBS/Tween, and incubated with biotinylated anti-mouse IgG and IgM (Jackson Laboratories, West Grove, Pa.) diluted 1:8000 in BBS. After one hour incubation with peroxidase labeled streptavidin (Kirkegaard & Perry, Gaithersburg, Md.) diluted to 1:2000 in BBS containing 1% BSA, the plates were washed 4 times with BBS/Tween, and incubated with TMB peroxidase substrate (Kirekegaard & Perry). Thirty minutes later absorption at 450 nm was measured in a TITERTEK MULTISCAN METER (Flow Laboratories, Rockville, Md.). Each assay included a standard mouse anti-KLH or anti-transferrin antiserum that was diluted serially starting at 1:5000. In the transferrin experiment, the absorption values were converted to relative antibody concentrations. In the descriptions of the results below, 1 is defined as the antibody level in a 1:5000 dilution of the standard antiserum.

Total IgG and IgG1 concentrations were determined in the transferrin experiment with radial immunodiffusion kits (The Binding Site, San Diego, Calif.), according to the manufacturer's instructions.

Antibodies to chromatin were assayed by ELISA, as described in the preceding examples. The ELISA OD values are referred to a standard curve that was established with a strongly positive reference serum. The results are the dilution of the standard curve which gave the same OD as the test sera $\times 10^6$, and have been shown to represent a linear measure of the amount of antibody present. The absolute units are arbitrary and are expressed in FIGS. 6 and 7 as equivalent dilution factors.

Measurement of Circulating Levels of TGF-β1 Protein. To determine whether gene administration leads to a sustained increase in circulating cytokine levels, mice were bled at week 6, four weeks after the 1st gene injection, and the plasma samples were assayed for TGF-β1 activity using the CCL64 mink lung cell proliferation assay, slightly modified as described in Latz, et al., *J. Immunol.*, 144:4189, which is incorporated herein by this reference. Rabbit antibody that specifically neutralizes TGF-β1, but not TGF-β2 or TGF-β3, was purchased from R&D Systems (Minneapolis, Minn.).

Measurement of Delayed Type Hypersensitivity Responses. To determine whether injection of cytokine genes modulates cellular immunity, delayed type hypersensitity (DTH) responses were tested by foot pad swelling 48 hours after antigen challenge. At day 70, 100 μg of transferrin in 100 μl of normal saline was injected into the right hind foot pad. Foot pad thickness was measured with calipers before and 48 hours after injection, and the difference between these measurements was calculated.

RESULTS

Figure 6A:
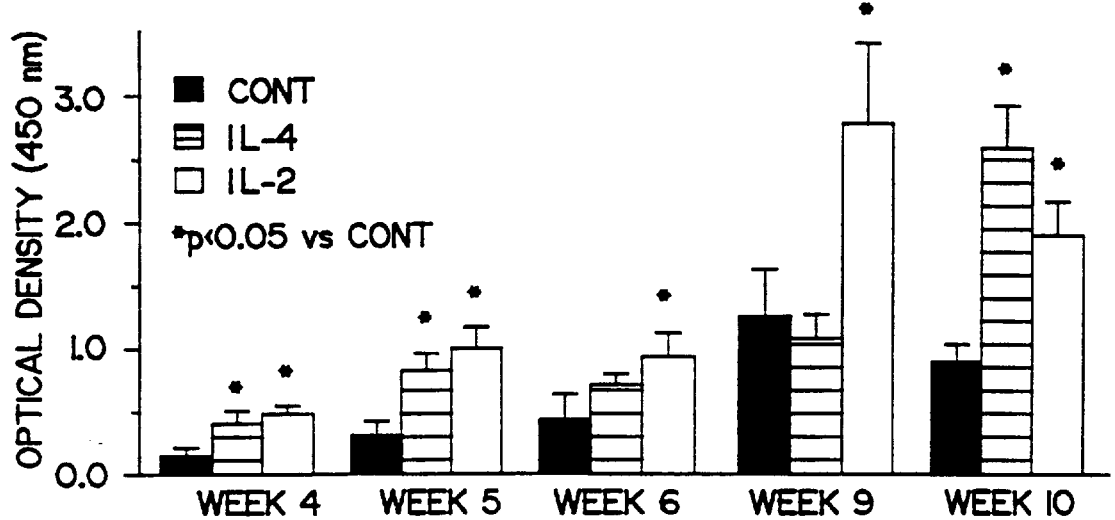
FIGS. 6A and 6B depict the results of ELISA's for ant-KLH levels in sera of mice injected intramuscularly with pRSVIL-2 and pRSVIL-4 (panel A) as well as pRSVTGFβ1 (panel B).
Figure 6B:
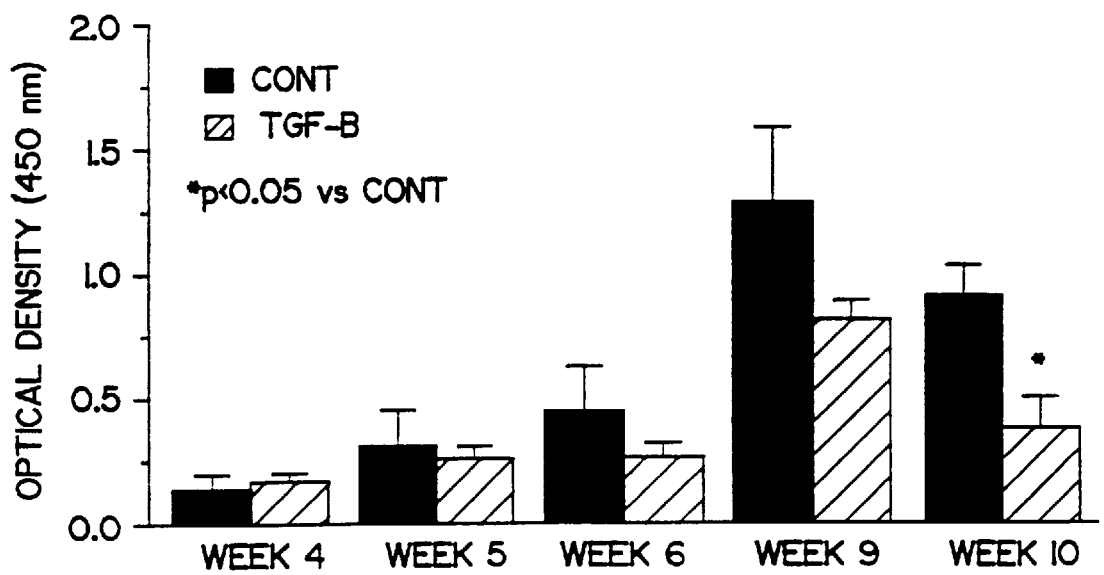
Figure 7A:
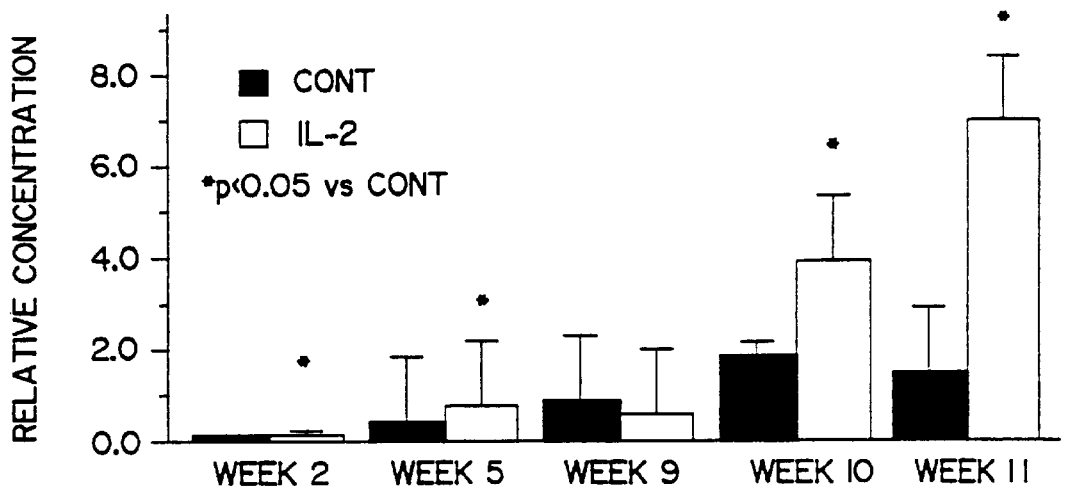
FIGS. 7A–7C depict the results of ELISA's for anti-transferrin levels in sera of mice following intramuscular injection of pRSVIL2 (panel A), pRSVTGFβ1 (panel B) and pRSVTGFβ (panel C).
Figure 7B:
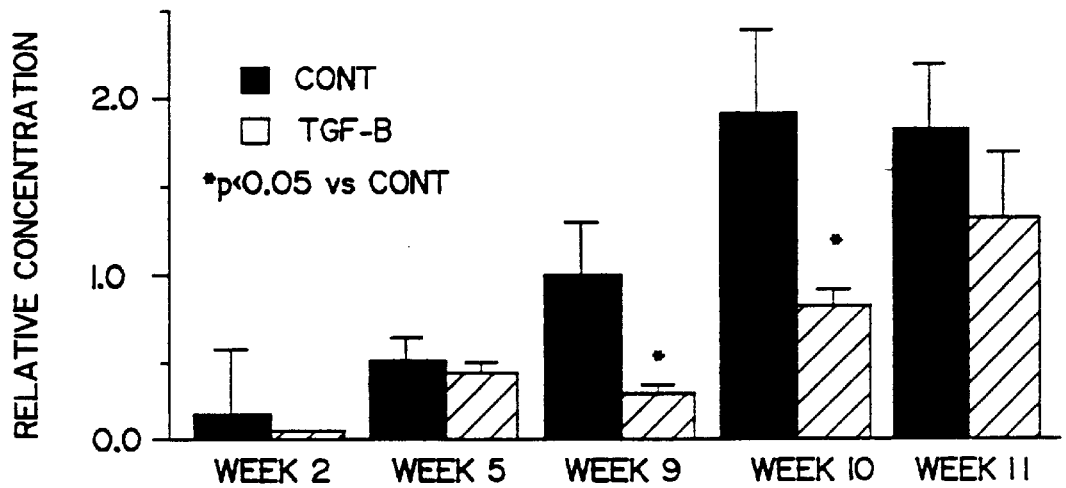
Figure 7C:
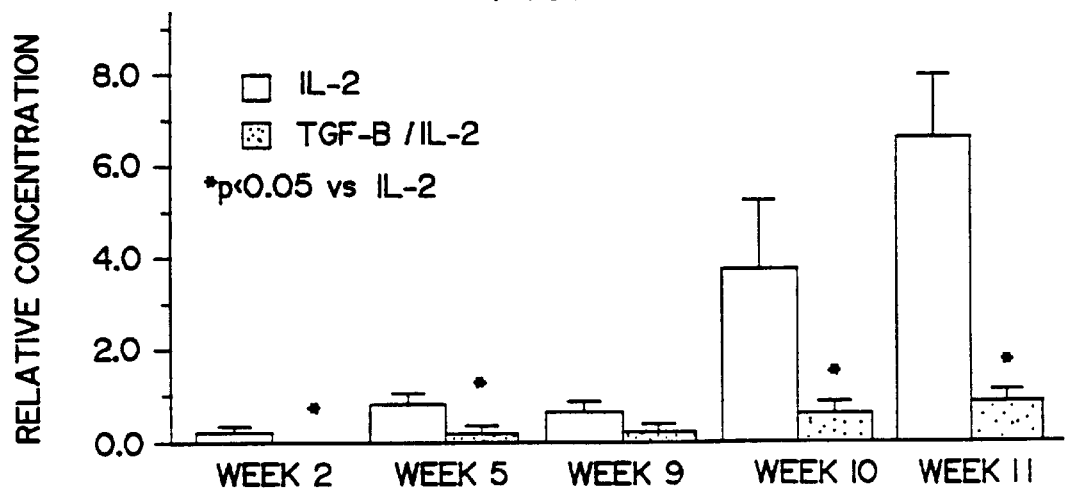

Effects of Cytokine Gone Injection on Antibody Responses to Foreign Antigens. In the first set of experiments, the effects of intramuscular cytokine gene injections on antibody responses to a foreign antigen, keyhold limpet hemocyanin (KLH), that was injected at the same site as the plasmid were determined. Antibodies to KLH reached higher levels in the pRSVIL2 and pRSVIL4 groups than in the control group (FIG. 6, panel A). In contrast, anti-KLH antibodies were lower in the pRSVTGFβ1 group than in the control group FIG. 6, panel B). To determine if the cytokine genes exerted their effects systemically, and not only at the regional lymph node, a second set of experiments was performed in which antigen (transferrin) and cytokine vectors were injected at two different sites. Antibodies to transferrin were highest in the pRSVIL2 group (FIG. 7, panel A), and were lowest in the pRSVTGFβ1 group (FIG. 7 panel B). These results showed that injection of the two plasmids was capable of stimulating or inhibiting the antibody response.

In several in vitro systems, TGFβ can antagonize the effects of IL-2. It is unknown whether TGFβ can have similar activities in vivo. Experiments were thus performed where plasmids encoding IL-2 or TGF-β1 were injected simultaneously. Anti-transferrin antibody levels in the group that received both pRSVIL2 and pRSVTGFβ1 were indistinguishable from the pRSVTGFβ group (FIG. 10 panel C), demonstrating that TGF-β1 expression completely neutralized the IL-2 effect. Mean anti-transferrin antibody levels in the pRSVIL4 group were higher but not significantly different from the control group (2.3±0.4 vs 1.7±0.36 mg/L in the 11th week).

Levels of Total IgG and IgG1. Levels of total IgG were measured in the sera from the transferrin injected mice. The highest IgG levels were observed in the pRSVIL2 and the pRSVIL4 groups after 10 and 11 weeks; the lowest levels were detected in the pRSVTGFβ1 group (Table I). TGF-β1 plasmid injections completely inhibited the IL-2 mediated increase. The levels of total IgG in the pRSVIL2/pRSVTGFβ1 group were similar to the pRSVTGFβ1 group. The mice injected with pRSVIL4 had significantly higher concentrations of IgG1 than the other groups.

TABLE I

|  | WEEK 5 | WEEK 10 | WEEK 11 |
|---|---|---|---|
| CONTROL | 1320 ± 75 (0.27)* | 2401 ± 121 (0.32)* | 3562 ± 167 (0.35)* |
| TGF-β | 1466 ± 76 (0.33)* | 2568 ± 252 (0.34)* | 3642 ± 171 (0.37)* |
| IL-2 | 1570 ± 95 (0.31)* | 2797 ± 153 (0.26)* | 3984 ± 163 (0.33)* |
| IL-4 | 2352 ± 207 (0.42) | 4033 ± 302 (0.39) | 4865 ± 343 (0.42) |

IgG1 levels were determined by radial immunodiffusion. Values are means ± SEM. The number in parentheses denote the ratio of IgG1/IGG at the same time point.
(*$p < 0.05$ vs. IL-4).

Figure 8:
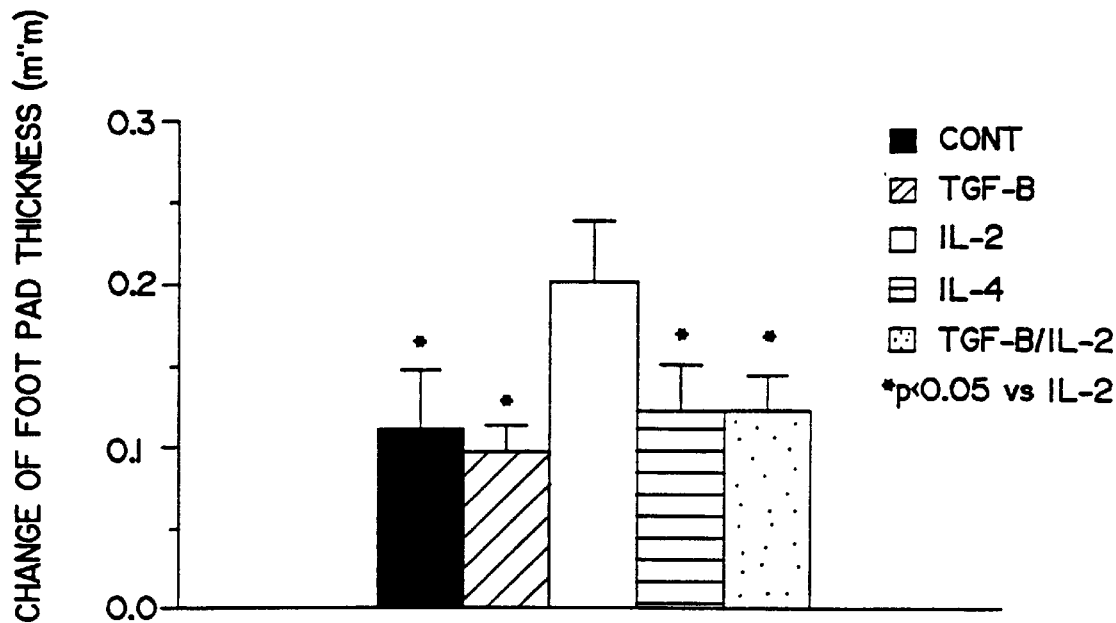
FIG. 8 depicts the results of a foot pad swelling assay after antigen challenge (in pRSVIL2 and pRSVTGFβ injected mice).

Delayed Type Hypersensitivity (DTH). To determine whether cytokine gene injections can modulate cellular immunity, DTH responses were tested by a foot pad swelling assay after antigen challenge. As shown in FIG. 8, there was a highly significant increase in foot pad swelling in pRSVIL2 injected mice, as compared to the control group. The co-injection of pRSVTGFβ1 completely inhibited the IL-2 effect Levels of Circulating TGF-β1. The mean plasma levels of TGF-β1 at week 6, four weeks after the last pRSVTGFβ1 injection, were 26 ng/ml as compared to only 0.32 ng/ml in the pRSVIL2 injected or untreated animals, which represents an 8 fold difference. The TGF-β activity was neutralized by specific antibodies to TGF-β1 (TABLE II).

TABLE II

| Plasmid | Total TGFβ Activity | TGF-β1 Activity |
|---|---|---|
| pRSV TGF-β1 | 2.6 ± 1.08 | 2.6 |
| pRSV IL-2 | 0.32 ± 0.11 | 0.32 |

Plasma samples from mice injected with either pRSV TGF-β1 or pRSV IL-2 were collected 4 weeks after the last plasmid injection. The samples were diluted 1:10, acidified to pH 4, neutralized and tested in triplicate in the CCL64 assay for TGF-β activity. Aliquots of the samples were also incubated with neutralizing rabbit antibody specific for TGF-β1 (10 ng/ml) prior to their addition to the CCL64 assay. Preimmune rabbit IgG did not change the levels of TGFβ activity. TGFβ levels were derived by comparison with a standard curve containing recombinant TGF-β1 (R&D Systems), are shown in ng/ml, and represent means ± SE from 3 samples per group.

Figure 9:
FIG. 9 depicts the results of ELISA's for anti-chromatin serum levels in pRSVIL-2 and pRSVTGFβ injected MRL/lpr/lpr mice.

Anti-Chromatin Antibodies. The results from the transferrin studies showed that plasmid DNA injections induced biological effects characteristic of the three cytokines during cellular or humoral immune responses to a foreign antigen. To determine whether this approach is also effective in modulating ongoing pathological immune responses, the IL-2 and TGF-β1 plasmids were introduced by i.m. injection into MRL/lpr/lpr mice, which produce high titers of autoantibodies and are used as a model of systemic lupus erythematosus. Titer of autoantibodies to chromatin in the MRL/lpr/lpr mice were significantiy increased in the pRSVIL2 group. The lowest titers were observed in the pRSVTGFβ1 group. The mean difference between the two groups was almost seven-fold (FIG. 9).

Gene expression in muscle tissue following injection of plasmid cDNA has been demonstrated previously by Wolff, et al., Nature, supra in experiments using reporter gene constructs. However, the results presented here are the first demonstration that direct injection of cDNA expression vectors into muscle can induce the production of biologically active proteins with systemic effects. Cytokine genes and antigens were injected into experimental animals at different times, and at disparate sites. Moreover, the immunologic actions of the cytokine genes persisted for weeks after administration. These results indicate that the effects of the cytokine genes were exerted systemically.

EXAMPLE V

PREVENTATIVE IL-2 GENE IMMUNOTHERAPY THROUGH SUBTHERAPEUTIC EXPRESSION OF A NAKED POLYNUCLEOTIDE IN A MOUSE LYMPHOMA MODEL (TO TEST IF THE EXPRESSED PROTEIN COULD PREVENT OR DELAY THE ONSET OF ILLNESS)

Experimental Design and Injection of Mice. Six-month-old AKR/J retired breeder female mice, 16 month old retired breeder female ICR outbred mice, 16 month old BALB/c old retired breeder female mice, and six-week-old BALB/c female mice were purchased from The Jackson Laboratory (Bar Harbor, Me.). AKR female mice have a 90% incidence of lymphoma by 9 months of age. Prior to experimentation, the AKR/J mice were pre-screened for the presence of circulating lymphoblastic cells by analysis of blood smear slides. The lymphoma-free animals were divided into two groups of twenty-three mice for DNA injection. AKR and ICR mice were given three weekly injections of DNA and then were subsequently injected biweekly throughout the experiments.

The cDNA for IL-2 was subcloned into the appropriate expression vectors as described in the preceding example. As described in previous examples, the vector referred to as pRSVIL-2, contains the IL-2 coding sequence (ATCC CRL #67618, Rockville, Md.) sandwiched between a Rous sarcoma virus long terminal repeat promoter sequence and a SV40 polyadonylation sequence.

The control vector, pRSV contains no IL-2 coding sequence. Plasmid DNAs were purified in large quantity using Promega MEGAPREP kits (Madison, Wis.). Purified plasmid DNAs (25 μg per injection) were suspended in 0.9% NaCl (100 μl per injection) and then were directly injected into the right quadricep muscles of each mouse with the use of a 28-gauge needle.

Expression and Detection of Protein. Serum samples were assayed for human IL-2 using an IL-2 ELISA kit from Advanced Magnetics, Inc. (Cambridge, Mass.). Each sample was assayed in duplicate and was compared to a standard curve using sera levels of recombinant human IL-2. The lower limit of detection in this assay is 75 pg/ml. Minimal cross-reactivity with mouse IL-2 was observed.

Figure 10:
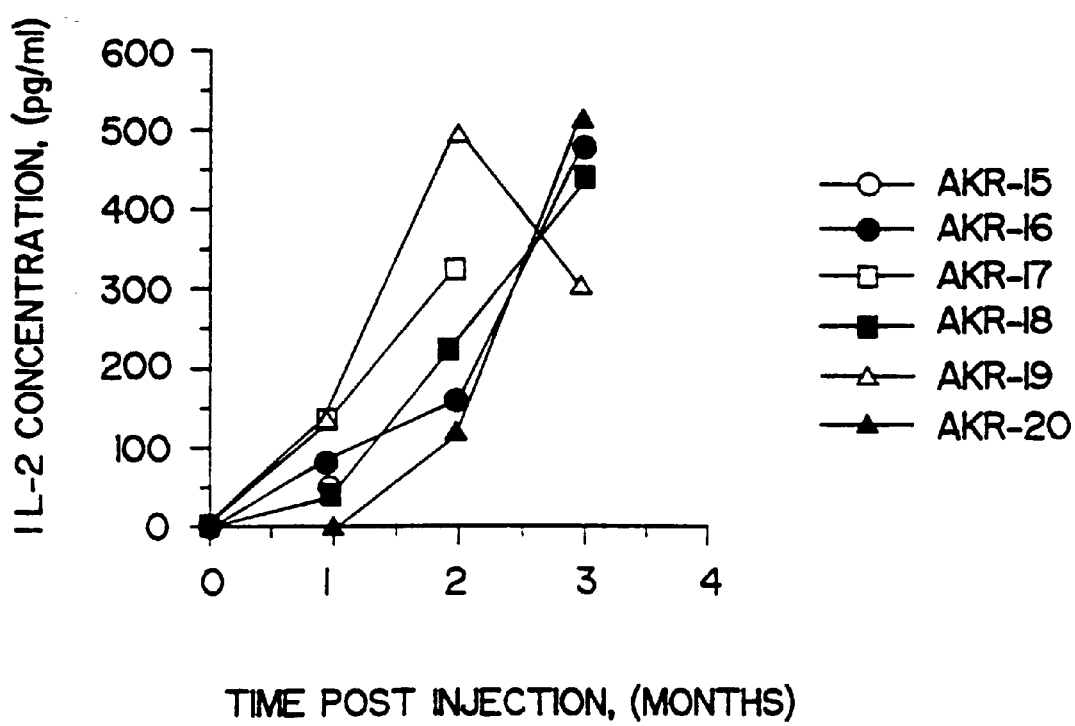
FIG. 10 depicts the results of ELISA's for IL-2 expression over time in individual AKR/J mice.

These results are reported in FIG. 10 (time course of expression in individual mice).

Effect on Animal Longevity. Survival of animals was measured from time of birth to time of sacrifice. Animals were sacrificed: a) after significant weight loss (i.e., >30% in a two week period, b) when hunching or breathing problems due to enlarged thymus appeared, or c) when massive numbers of lymphoblastic cells in peripheral blood. In general, peripheral lymphoblastic cell appeared emergence and physical signs of deterioration became detectable between 7 to 10 days prior to death.

Statistics of the survial curve data were performed using the Kaplan-Meyer Survival Curve estimator well-known in the art. The significance between the groups was determined using the Mantel-Haentzel test well-known in the art.

Figure 11:
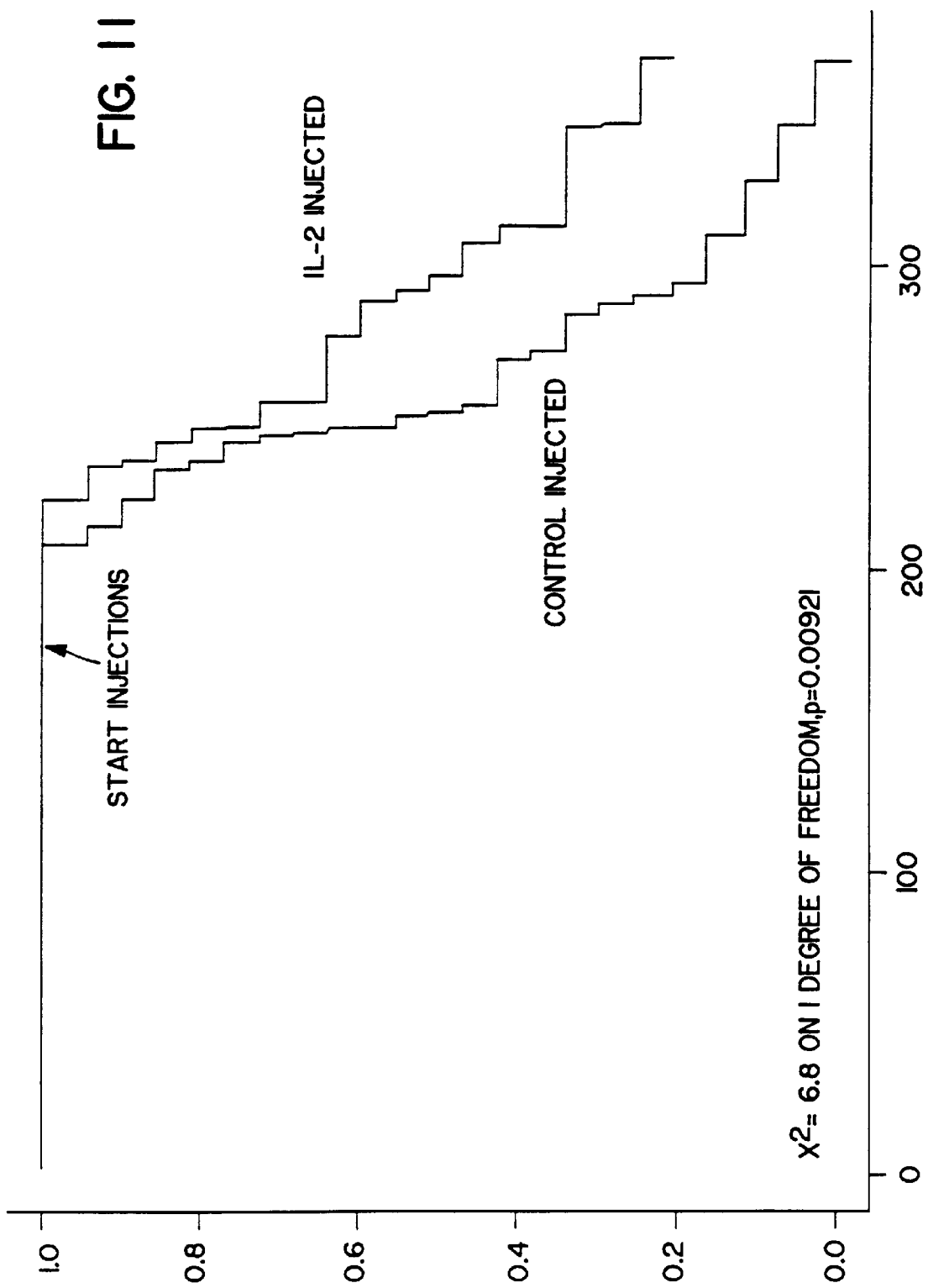
FIG. 11 depicts longevity data for the mice described with respect to FIG. 10.

The data regarding longevity of the animals used in this experiment are summarized in FIG. 11. Half of the animals in the control group were dead in seven months and twenty days of lymphoma and all were dead in 9 months. In contrast, four of the six animals which received naked pRSVIL-2 were alive at 9 months.

Analysis of Natural Killer (NK) Cell Populations to Determine Impact of IL-2 Gene Expression on Cytolytic Activity Against Lymphoblastic Cells in Young AKR/J Mice. Natural killer cytolytic activity in the injected mice was measured using the standard $^{51}$Cr-release assay known in the art. YAC1 (an NK-sensitive Moloney murine leukemia virus-induced mouse lymphoma cell line) and P815 (an NK-resistant murine mastocytoma cell line) were obtained from the ATCC (Rockville, Md.) and used as target cells. $^{51}$Cr-labeled target cells were added to wells of round-bottom 96-well microtiter plates, and effector cells were plated in triplicate to yield various effector to target (E/T) ratios. Nonadherent mouse PBL's (effector cells) were isolated by Lymphocyte M (Cedarlane Laboratories Ltd., Homby, Ontario) gradient centrifugation and were depleted for mononuclear cells by incubation overnight in culture dishes. Effector and target cells were coincubated for 4 hours. Supernatants were harvested and counted in a gamma counter for determination of isotope release.

Figure 12:
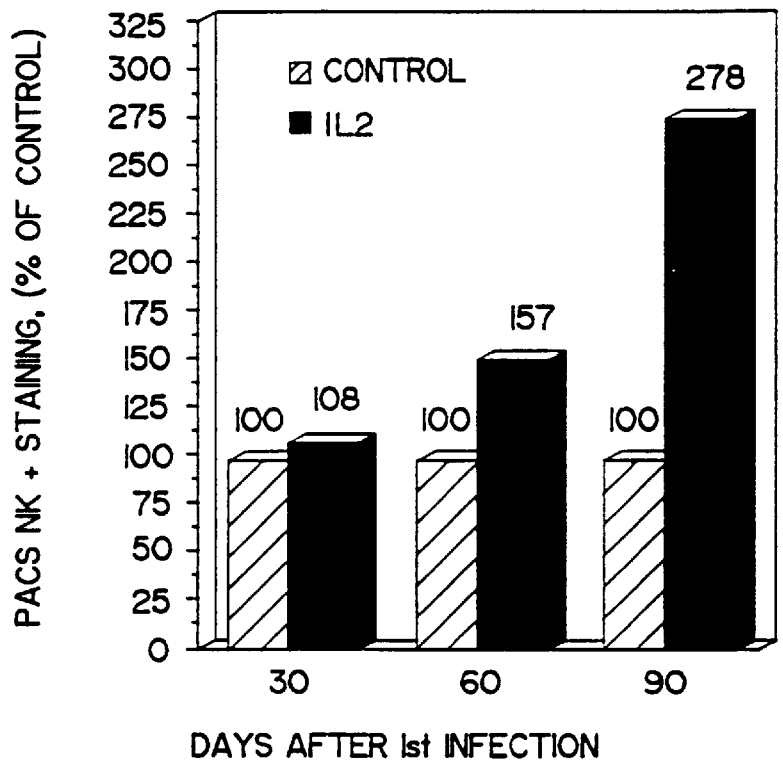
FIG. 12 depicts the results of a $^{51}$Cr-release assay for NK cell cytolytic activity in AKR/J mice (mouse lymphoma model following introduction of a naked polynucleotide at a dosage sufficent to produce IL-2 gene expression at sub-therapeutic levels.

Results are expressed in FIG. 12 as percent specific $^{51}$Cr release as calculated from the following formula: 100× [(mean cpm experimental−mean cpm spontaneous release) (mean cpm total release−mean cpm spontaneous release)]. Values shown are mean+. SEM for all samples at a specified E/T ratio, and at the time point indicated. Spontaneous release was measured after addition of 2% SDS. The results of this assay confirm natural killer activity against lymphoblastic cells in AKR/J mice which received the injections of plasmid. This activity would normally be substantially absent in these mice.

EXAMPLE VI

RESPONSES TO VARIATIONS IN DOSAGE LEVELS FOR INTRODUCTION OF NAKED IL-2 GENES INTO YOUNG AND AGED MICE

Using Balb/c mice and the plasmids described in Example V, pRSVIL2 in 0.9% saline was injected into separate mice weekly at dosages of, respectively, 0 (i.e., pRSV only), 5, 12.5, 25, 50 and 100 μg per injection. For each dosage, three younger (about 16 weeks) and three older (16 months old or older) mice are injected in the right hind leg muscle.

Figure 13A:
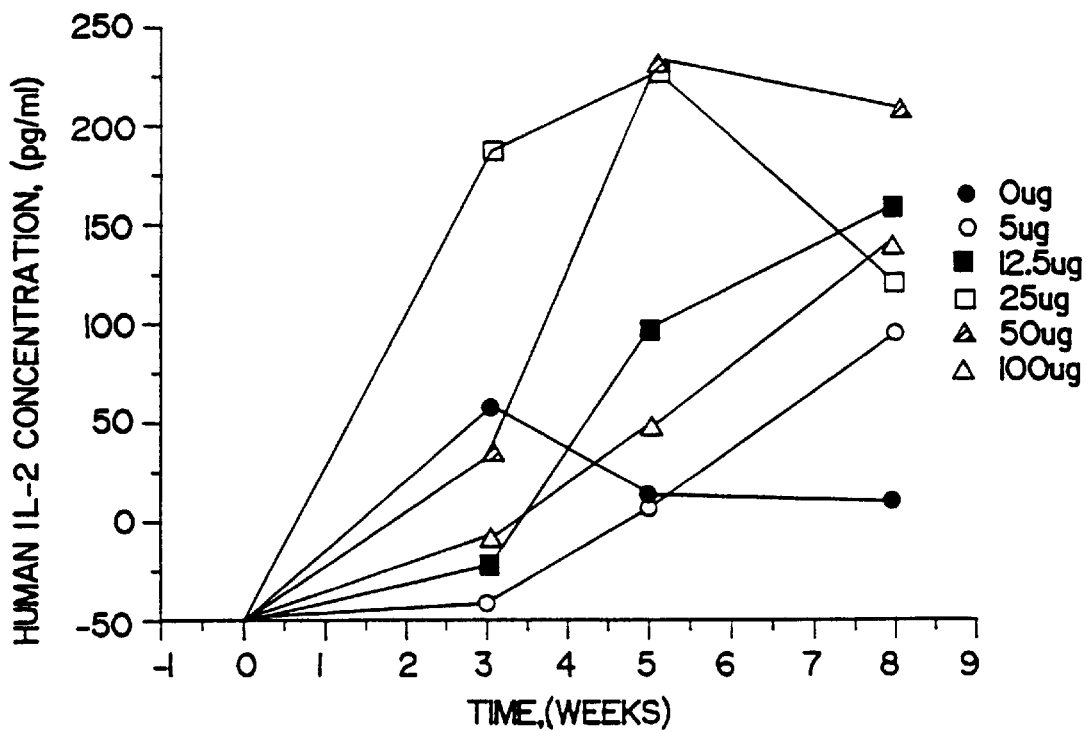
FIGS. 13A and 13 B depict the levels of IL-2 expression in following administration of naked pRSVIL-2 in different dosages to young Balb/c mice and older Balb/c mice.
Figure 13B:
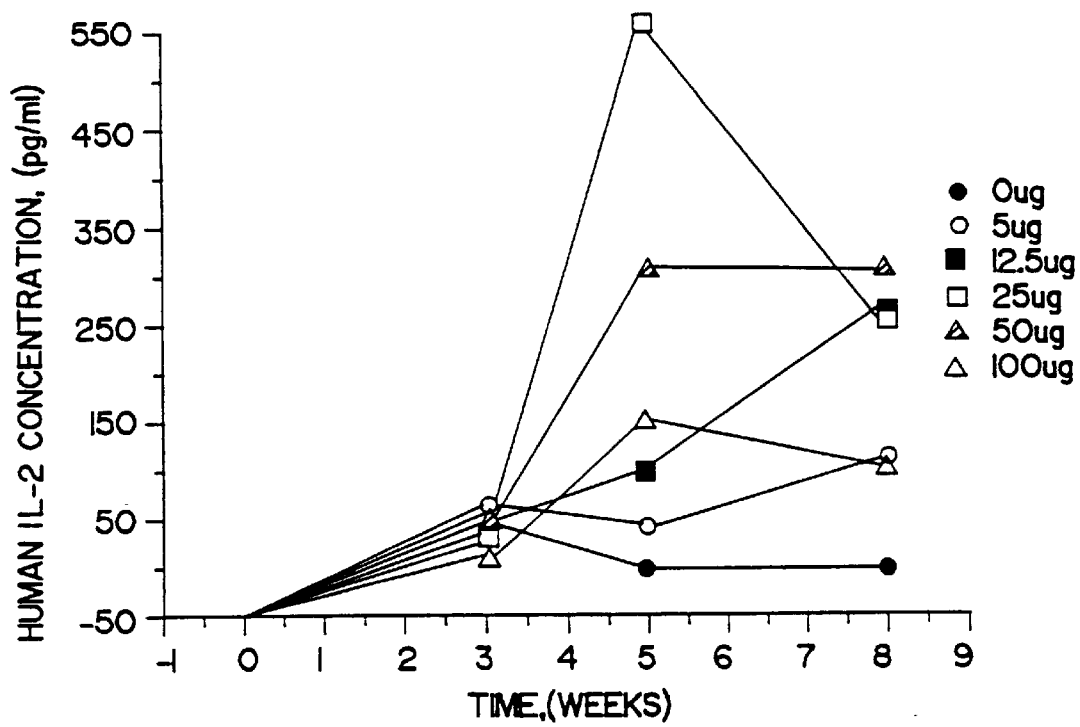

IL-2 expression was assayed in each group of mice as described in Example V. These data are shown in FIGS. 13(a)–(b). The weight and physical appearance of the animals were also monitored for signs of toxicity. Some toxicity was apparent at the 50 and 100 μg dosage levels tested.

Maximal results in these mice were achieved at 12.5–25 μg/100 ml of 0.9% saline. Expression was slightly greater in the older mice at 1 month, but was slightly greater at two weeks in the younger mice.

EXAMPLE VII

SYSTEMIC EXPRESSION FOLLOWING INTRODUCTION OF NAKED POLYNUCLEOTIDES THROUGH DIFFERENT POINTS OF ENTRY

Groups of young Balb/c mice were injected at weekly intervals with naked pRSVIL2 either (1) subcutaneously (back), (2) intramuscularly (right hind leg), (3) intradermally (base of the tail), or (4) intranasally. The plasmids used were as described in Example V.

Figure 14:
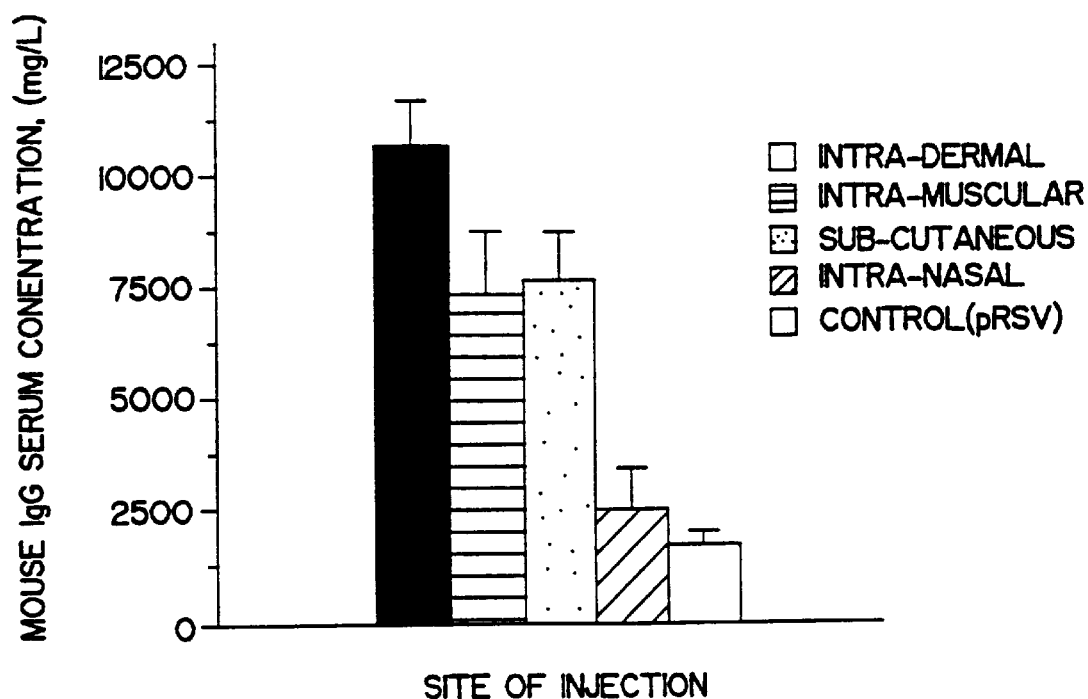
FIG. 14 depicts the levels of IL-2 expression detected in sera following pRSVIL-2 administration at different points of entry.

The data regarding the levels of systemic expression achieved from administration of naked pRSVIL2 via each of these routes are shown in FIG. 14.

EXAMPLE VIII

CORRELATION OF HUMAN IL-2 OR EXPRESSION IN ICR MICE WITH THE SPECIFIC STIMULATION AND EXPANSION OF THE MOUSE NATURAL KILLER CELL POPULATION

In the AKR cancer model, it is believed that a specific expansion or stimulation of the natural killer cell population in the IL-2 injected mice is the factor that confers the beneficial effect to this group towards tumor cells immunosurveillance. In Example V, IL-2 levels (as measured by ELISA) were therefore correlated with natural killer activity. Both values increased significantly compared with the values from the control-injected group, which increase was experienced during the same time interval (0 to 3 months of injection). At the same time, no changes in the levels of peripheral lymphocytes or granulocytes were detected by analysis of blood smear slides in the treated animals. This finding is significant because it indicates that no inflammation occurred after injections and that subsets of the immune system other than NK cell population were unaffected by the levels of IL-2 expression after injections.

The same information was sought in aged animals as follows:

Each group of animals contained ten aged ICR (an outbred mouse strain without inherent pathology) mice. Animals were injected with pRSV or pRSV-IL-2 using the same protocol as the AKR animals in the preceding examples. The relative white blood cell counts in these animals (0 to 4 months after injection) was measured. The results are shown in Table II below:

TABLE III

| Injection | Relative White Blood Cell Count | | | | |
|---|---|---|---|---|---|
|  | 0 | 1 | 2 | 3 | 4 |
| pRSV | 100 | 98 | 91 | 132 | 92 |
| pRSV-IL2 | 100 | 94 | 88 | 81 | 98 |

NK cell activity was measured with a $^{51}$Cr-release assay as described in Example V. Target cells were either p815 (NK-resistant mouse mastocytoma) or YAC-1 (NK-sensitive mouse lymphoma). Effector cells were isolated by lymphocyte M centrifugation. The formula used to measure NK cell activity is:

$$\% \text{ release} = \left( \frac{\text{Experimental release} - \text{spontaneous release}}{\text{Maximal release} - \text{spontaneous release}} \right) \times 100$$

These data are presented in Table IV below.

TABLE IV

| Injection | % Lysis P815 | % Lysis YAC-1 |
|---|---|---|
| pRSV (E/T = 25:1) | 2.6 | 11.1 |
| pRSV (E/T = 100:1) | 1.6 | 10.1 |
| pRSV-IL2 (E/T = 25:1) | 10.9 | 31.8 |
| pRSV-IL2 (E/T = 100:1) | 5.3 | 25.7 |

EXAMPLE IX

HISTOLOGICAL STUDIES SHOWING CELL UPTAKE OF NAKED POLYNUCLEOTIDES BY MONONUCLEAR CELLS AT THE POINT OF ENTRY IN SKIN

Three days after intradermal injection of the tails of naked pCMV/acz into Balb/c mice, the mice were sacrificed. Tissue cultures were obtained at the point of entry for the plasmid and stained for *E. coli* β-galactosidase activity. A photograph (40× magnification) of a slide from the histological examination of these cultures is contained in FIG. 15.

Figure 15:
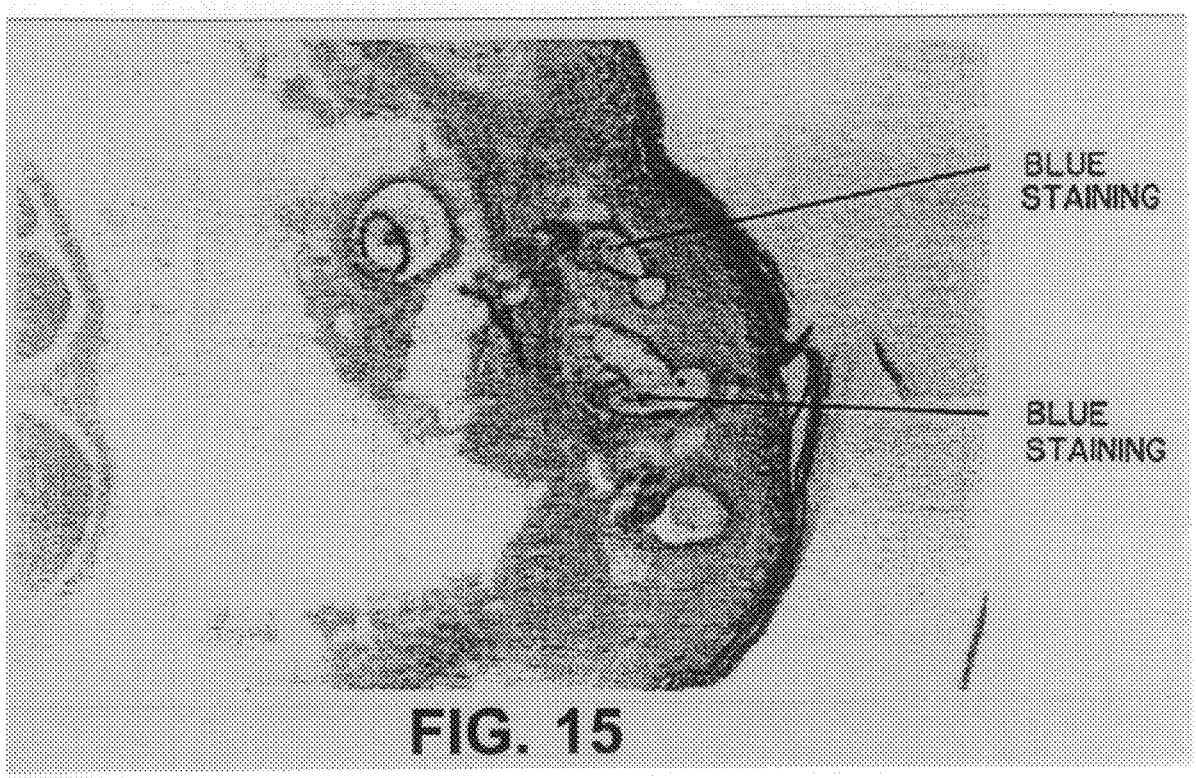
FIG. 15 is a photograph of the results of histological studies of skin at the point of entry for pCMVRNP in Balb/c mice showing uptake of the plasmid by mononuclear cells (APC's). An APC is indicated by an arrows; a tissue cell (not containing the plasmid) is indicated by a slashed line.

As shown in FIG. 15, uptake of the plasmid is shown (in blue) to be by mononuclear cells. The fibroblasts in the tissue samples are not stained, thus indicating that the plasmid was not taken up by these cells. The rounded, mononuclear cells which did take up the plasmid appear to be macrophages and/or other antigen presenting cells, which would indicate that uptake of the plasmid is by phagocytosis.

EXAMPLE X

EPIDERMAL ADMINISTRATION OF A NAKED POLYNUCLEOTIDE USING A MECHANICAL IRRITANT TO ELICIT AN IMMUNE RESPONSE

Figure 16:
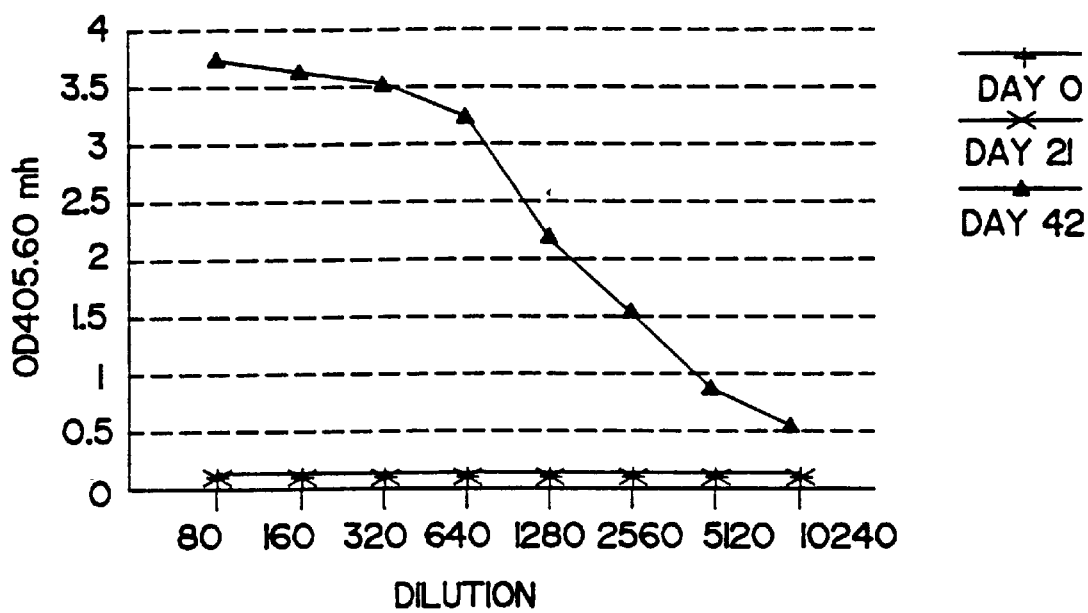
FIG. 16 depicts the results of an ELISA for anti-NP IgG following mechanical epidermal administration of naked pCMVRNP to Balb/c mice.

FIG. 16 depicts the results of an ELISA performed as described in Example I for serum levels of anti-NP IgG following epidermal administration of pCMVRNP via mechanical means.

The plasmid was coated onto the tynes of an uncoated MONO-VACC device as described supra. (It should be noted that it is alternatively possible for the naked polynucleotides to be lyophilized onto the tynes of the device for longer storage stability). Total plasmid concentration on all of the device tynes was approximately 50 μg in an isotonic normal saline carrier (approximately 150 μg plasmid per milliliter). The back of a Balb/c mouse was shaved and the shaved skin gently scratched with the tyne device. As shown in FIG. 16, anti-NP IgG were subsequently detected in serum (e.g., at day 42, the serum from this mouse contained antibodies at a titer of 1:10240).

EXAMPLE XI

EPIDERMAL ADMINISTRATION OF A NAKED POLYNUCLEOTIDE USING A CHEMICAL AGENT TO ELICIT AN IMMUNE RESPONSE

Figure 17:
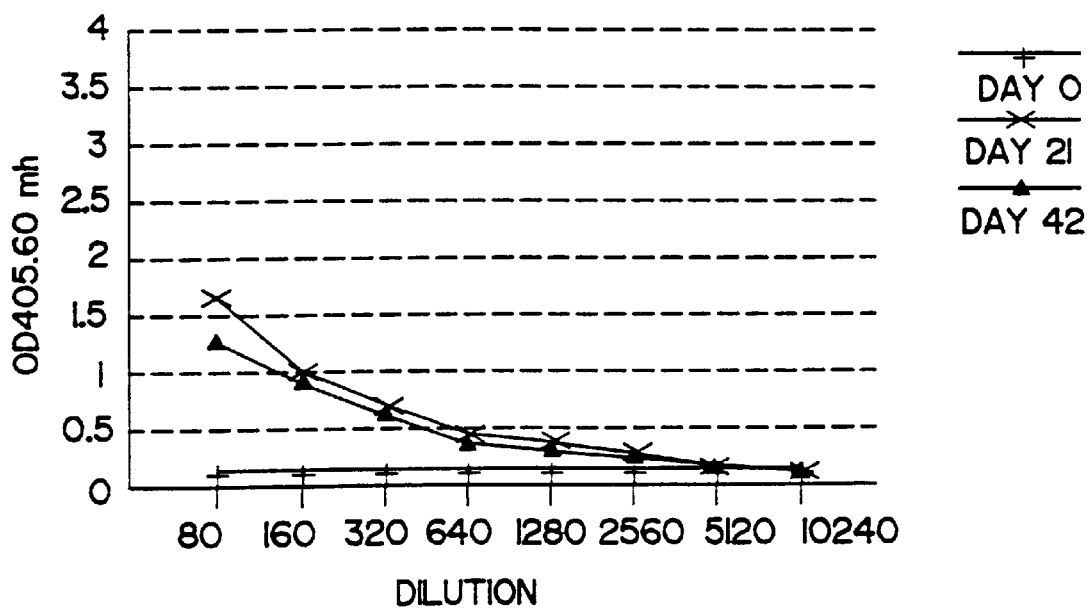
FIG. 17 depicts the results of an ELISA for anti-NP IgG following chemical epidermal administration of naked pCMVRNP to Balb/c mice.

FIG. 17 depicts the results of an ELISA performed as described in Example I for serum levels of anti-NP IgG following epidermal administration of pCMVRNP in conjunction with the application of a chemical agent.

The plasmid was suspended in 40 μg of an isotonic normal saline solution containing approximately 150 μg of plasmid per milliliter. This solution was absorbed onto the nonadhesive pad of a BAND-AID brand bandage (Johnson & Johnson).

A Balb/c mouse was shaved as described in Example X and a commercially available keratinolytic agent (here, the previously described depilatory creme sold under the tradename NAIR) was applied to the shaved skin. After several minutes, the keratinolytic agent was washed off of the skin and the plasmid-containing bandage applied thereto. As shown in FIG. 17, the treated animal developed serum anti-NP IgG at a titer of 1:640.

EXAMPLE XII

STABILITY OF IL-2 EXPRESSION FOLLOWING ADMINISTRATION OF NAKED pRSV-IL-2

Figure 18:
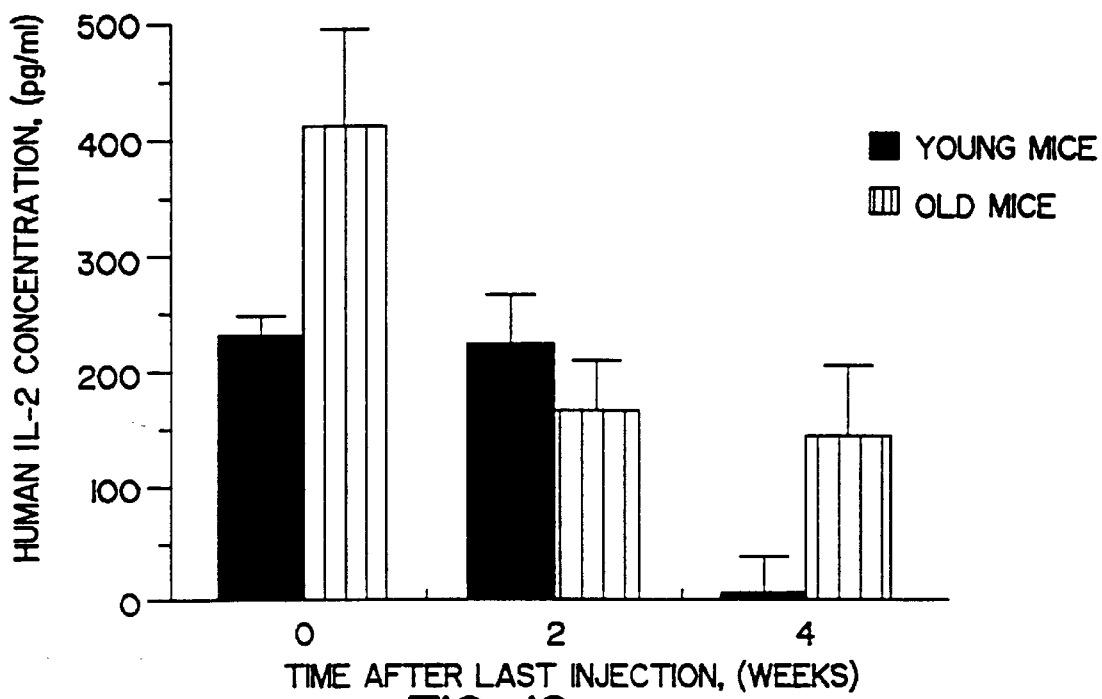
FIG. 18 depicts the stability of IL-2 expression detected in sera over time after administration of a naked polynucleotide encoding IL-2.

Stability of IL-2 expression was measured in the mice described with respect to Example VII. After two weekly injections of pRSV-IL2, serum levels of IL-2 were measured as described in Example V. In older mice, serum levels of IL-2 declined more slowly than in younger mice. These data are shown in FIG. 18 and demonstrate that relatively stable gene expression can be achieved via introduction of naked polynucleotides to tissues having a relatively high concentration of APC's therein, particularly as compared to muscle tissue.

EXAMPLE XIII

IMMUNE RESPONSE TO VIRAL CHALLENGE BY MICE INTRADERMALLY INJECTED WITH NAKED pCMVRNP

To test whether immunity generated by vaccination with appropriate naked polynucleotides could protect animals from a lethal viral challenge, groups of 10 Balb/c mice were injected intradermally 3 times with 15 μg of a pCMVRNP plasmid which contained the NP gene from an H1N1 strain of influenza virus (A/PR/8/34; provided by Dr. Inocent N. Mbawvike at the Baylor College of Medicine, U.S.) Control groups included uninjected animals as well as animals injected with an irrelevant plasmid (pnBL3).

Figure 19:
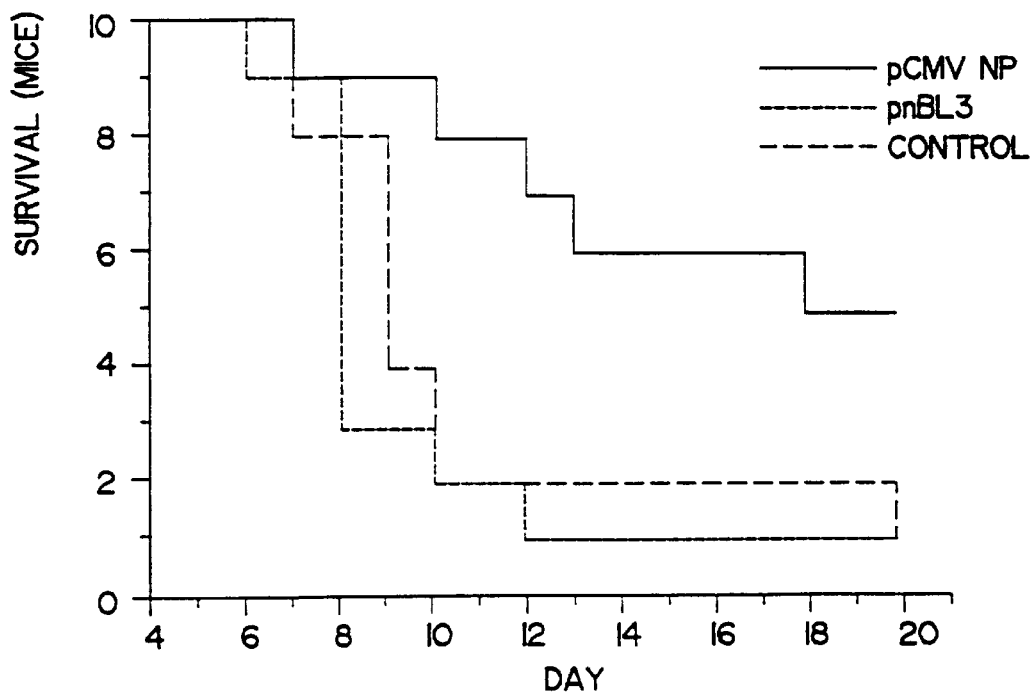
FIG. 19 contains a Kaplan-Meyer survival curve depicting the length of time that Balb/c mice injected intradermally with naked pCMVRNP survived following viral challenge.

Six weeks after the initial plasmid injections, the animals were challenged with a $LD_{90}$ dose of an H3N2 influenza strain (A/HK/68); also provided by Dr. Mbawuike). Intradermally vaccinated mice were significantly protected from the challenge (P<0.01) as compared to unvaccinated control mice; see FIG. 19 (a Kaplan-Meyer survival curve).

EXAMPLE XIV

RELATIVE LEVELS OF GENE EXPRESSION FOLLOWING INTRADERMAL INJECTIONS OF NAKED CYTOMEGALOVIRUS OR ROUS SARCOMA VIRUS PROMOTER-CONTAINING NAKED PLASMIDS

Figure 20:
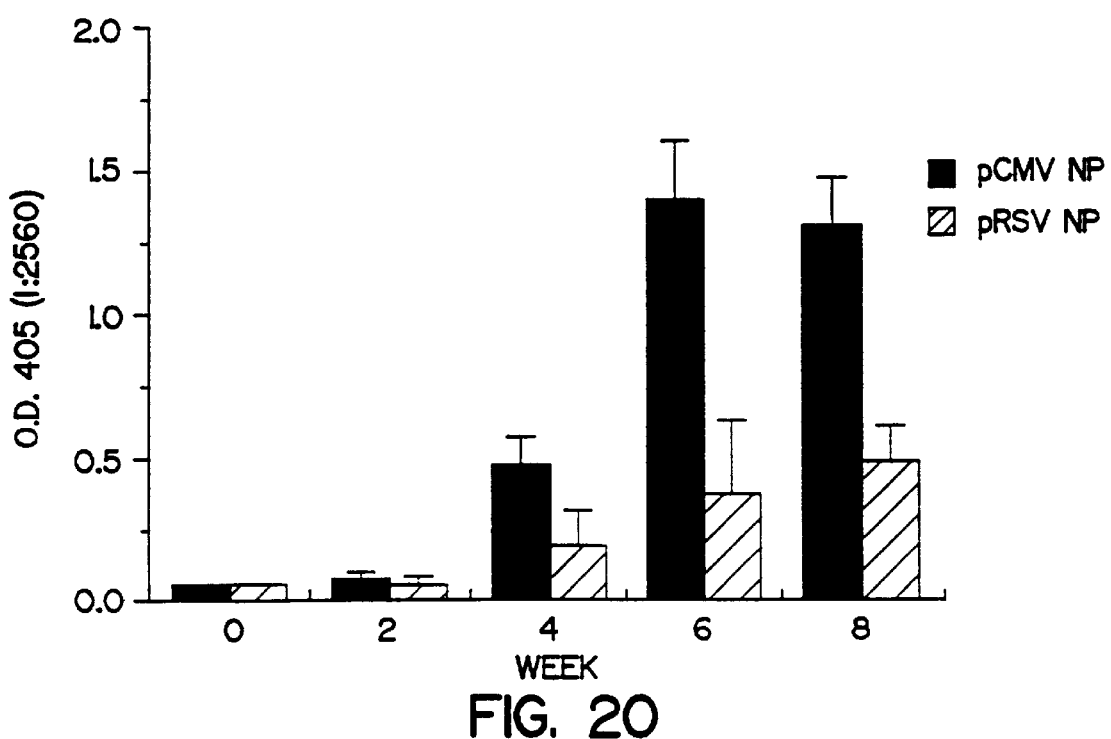
FIG. 20 graphically compares NP gene expression following separate intradermal injections of naked plasmids containing either a CMV or an RSV promoter sequence.
Figure 21A:
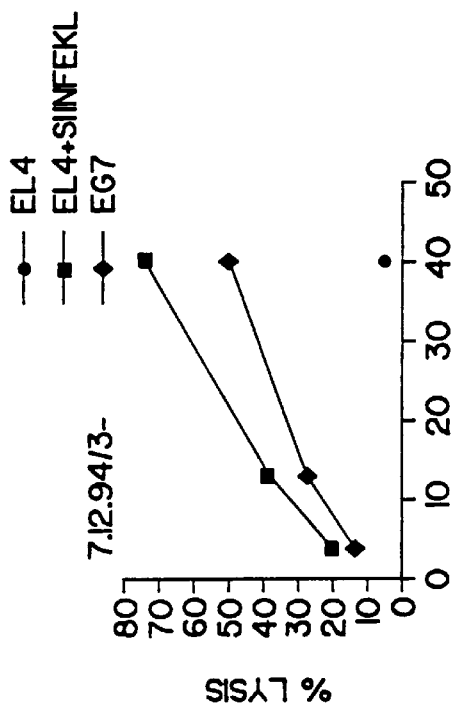
Figure 21B:
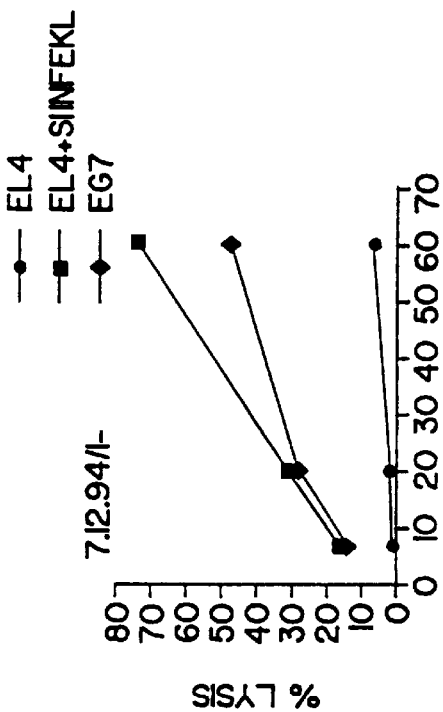
Figure 21C:
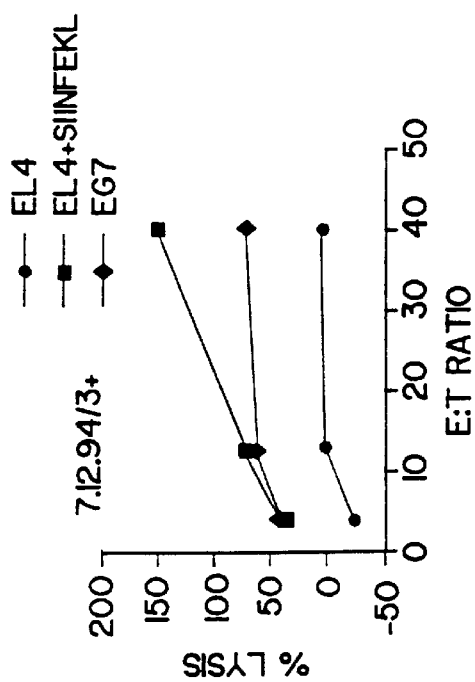
Figure 21D:
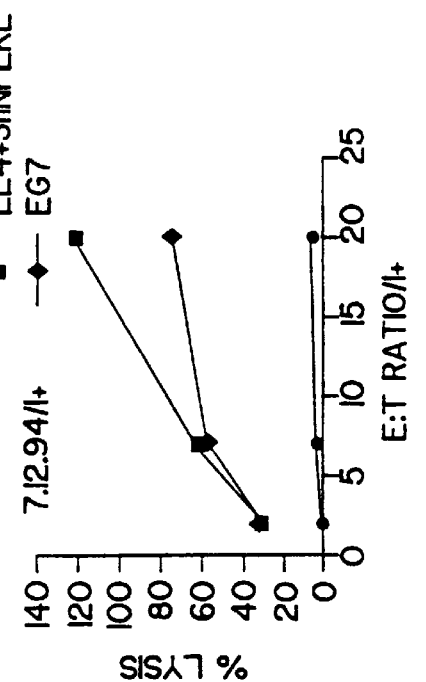

The possible effect of the promoter region used in an expression vector was evaluated by testing two plasmids which contain the RNP gene described in Example II. One plasmid, pCMVRNP, contained the cytomegalovirus immediate early promoter, enhancer and intron region. The other plasmid contained the promoter from the Rous sarcoma virus LTR region (pRSVRNP). As shown in FIG. 20, antibody responses to the NP protein expressed by the plasmids were consistently higher with the CMV promoter after intradermal injections. This contrast with the responses seen after intramuscular injection of the NP gene, where antibody levels produced by the two plasmids are essentially equivalent (data not shown).

EXAMPLE XV

SELECTIVE INDUCTION OF CYTOTOXIC T LYMPHOCYTE RESPONSES AFTER INTRADERMAL ADMINISTRATION OF NAKED POLYNUCLEOTIDES

Mice of the C57/B6 strain were injected intradermally in the tail at two week intervals with 100 μg naked DNA purified from a CDM8 ova plasmid (described in detail in Shastri, et al., *J.Immunol.*, 150:2724–2736, 1993). The CDM8 ova plasmid contains the full length (1.8 kb) cDNA for ovalbumin.

2 weeks after the second gene adminstration, the spleens of the mice wre removed and cultured in vitro with lethally irradiated (3000 rad) syngeneic splenocytes that had been pulsed with a synthetic ovalbumin peptide. This peptide is a class I restricted target for cytotoxic T cells in mice with the histocompatibility haplotype $K^b$ described by Shastri, et al.

After five days of culture, the cells were incubated with targets of 2 types to test for the generation of cytotoxic T cells by the mice who had received the gene encoding ovalbumin. The targets were mouse EL-4 lymphocytes pulsed with the synthetic ovalbumin peptide, or EL-4 cells that had been stably transfected with the cDNA for ovalbumin (see, FIG. 21; the cDNA for ovalbumin is designated as "EG7" in the FIGURE). The percent lysis of the 2 targets was determined for different effector-to-target ratios (designated as "E:T ratio" in FIG. 21). As shown in FIG. 21, the animals that received the naked CDM8 ova plasmid had produced cytotoxic T cells that were specific for the ovalbumin targets (i.e., for EL-4 with the ovalbumin peptide and for EG7), but were not specific for the control EL-4 cells (i.e., those without the ovalbumin peptide).

C57/B6 mice vaccinated intradermally with CDM8 ova plasmids were also screened for antibodies to ovalbumin. Sera collected 6 weeks after administration of the CDM8 ova plasmids did not contain any detectable levels of antibody (as measured using an enzyme-linked immunoabsorbent assay on microtiter plates coated with ovalbumin). Collectively, these data indicate that the methods for administration of naked polynucleotides of the invention will induce MHC class I restricted cytotoxic T cells (here, to ovalbumin) without inducing antibody production.

EXAMPLE XVI

PROLONGED IMMUNOLOGIC MEMORY AFTER INTRADERMAL ADMINISTRATION OF NAKED POLYNUCLEOTIDES INDUCED BY ANTIGEN STIMULATION OF T CELLS 0.1, 1, 10 and 100 μg of naked polynucleotides in plasmid form (0.5–5 ng/1 mg DNA endotoxin content) encoding the *E.coli* enzyme β-galactosidase under the control of the CMV promoter ("pCMV Lac-Z") were administered to groups of 4 mice\dosage\route either intramuscularly ("IM") or intradermally ("ID"). For comparison, another group of 4 mice\dosage received 100 μg β-galactosidase protein ("PR") intradermally. All injections were made using 50 μl normal saline as carrier. IM and ID injections were made with a 0.5 ml syringe and a 28.5 gauge needle. Antibodies were thereafter measured by enzyme-linked immunoabsorbent assay at 2 week intervals.

Briefly, total antibodies were measured using β-galactosidase (Calbiochem, Calif.) as the solid phase antigen. Microtiter plates (Costar, Cambridge, Mass.) were coated with 5 μg of antigen dissolved in 90 mM borate (pH 8.3) and 89 mM NaCl (i.e., borate buffered saline; BBS) overnight at room temperature and blocked overnight with 10 mg/ml of bovine serum albumin in BBS.

Serum samples were serially diluted in BBS starting at a 1:40 dilution for the first 8 weeks, them a 1:320 dilution thereafter. These samples were added to the plates and stored overnight at room temperature. Plates were washed in BBS+ 0.05% polysorbate 20, then reacted with a 1:2000 dilution of alkaline phosphatase labeled goat anti-mouse IgG antibody (Jackson Immunoresearch Labs., West Grove, Pa.) for 1 hour at room temperature, or were reacted with a 1:2000 dilution of alkaline phosphatase labeled goat anti-mouse IgG 1 antibody (Southern Biotech of Alabama), or were reacted with a 1:500 dilution of alkaline phosphatase labeled rat anti-mouse IgG 2A antibody (Pharmingen, of California), under the same conditions. Plates were washed again, then a solution of 1 mg/ml of p-nitrophenol phosphate (Boehringer-Mannheim, Indianapolis, Ind.) in 0.05 M carbonate buffer (pH 9.8), containing 1 mM $MgCl_2$ was added. Absorbance at 405 nm was read 1 hour after addition of substrate to the plates.

Figure 22:
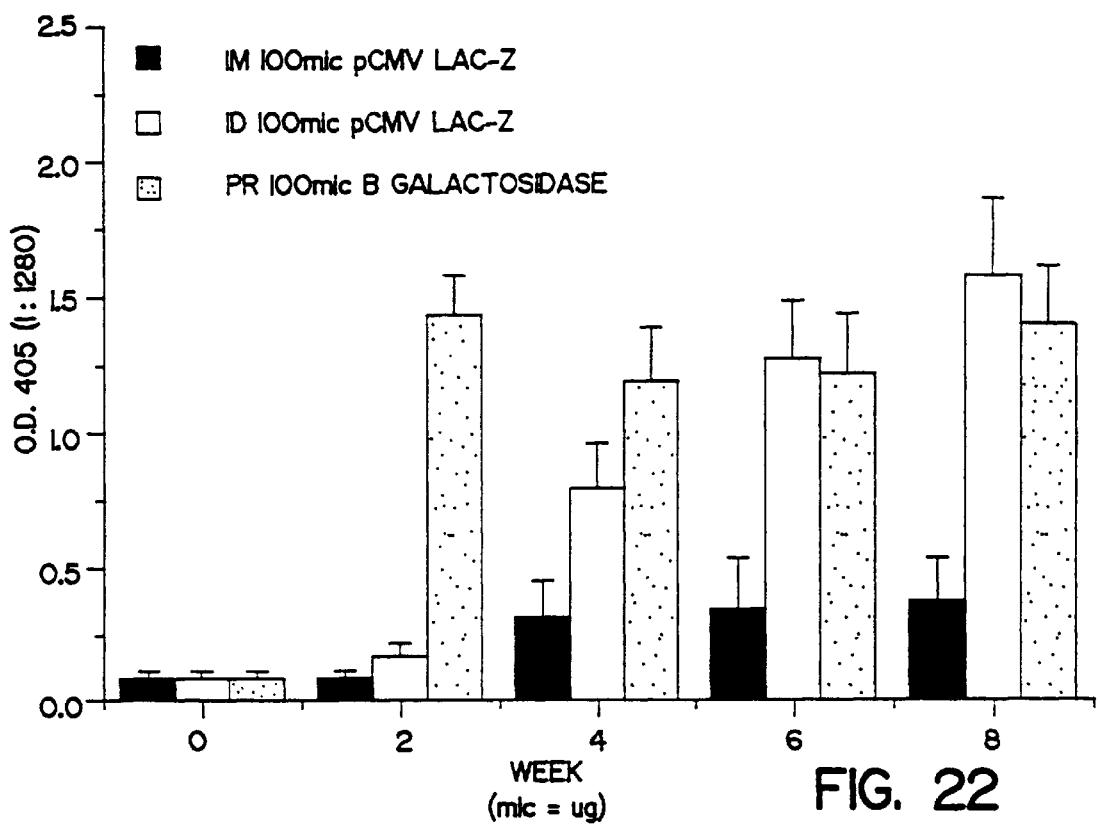

As shown in FIG. 22, antibody responses of equivalent magnitude were induced in the animals who had received the pCMV Lac-Z plasmids by ID injection and the amimals who had received the PR, while lesser antibody responses were measured in the animals who had received the pCMV Lac-Z plasmids by IM injection.

To assess for T cell memory, the animals were then boosted with 0.5 μg of PR at a separate site by ID injection. If these animals had developed memory T cells to control production of antibody to β-galactosidase, they would be expected to mount a more vigorous immune response after boosting with soluble protein antigen than had been demonstrated in response to the priming dose of antigen.

Figure 23:
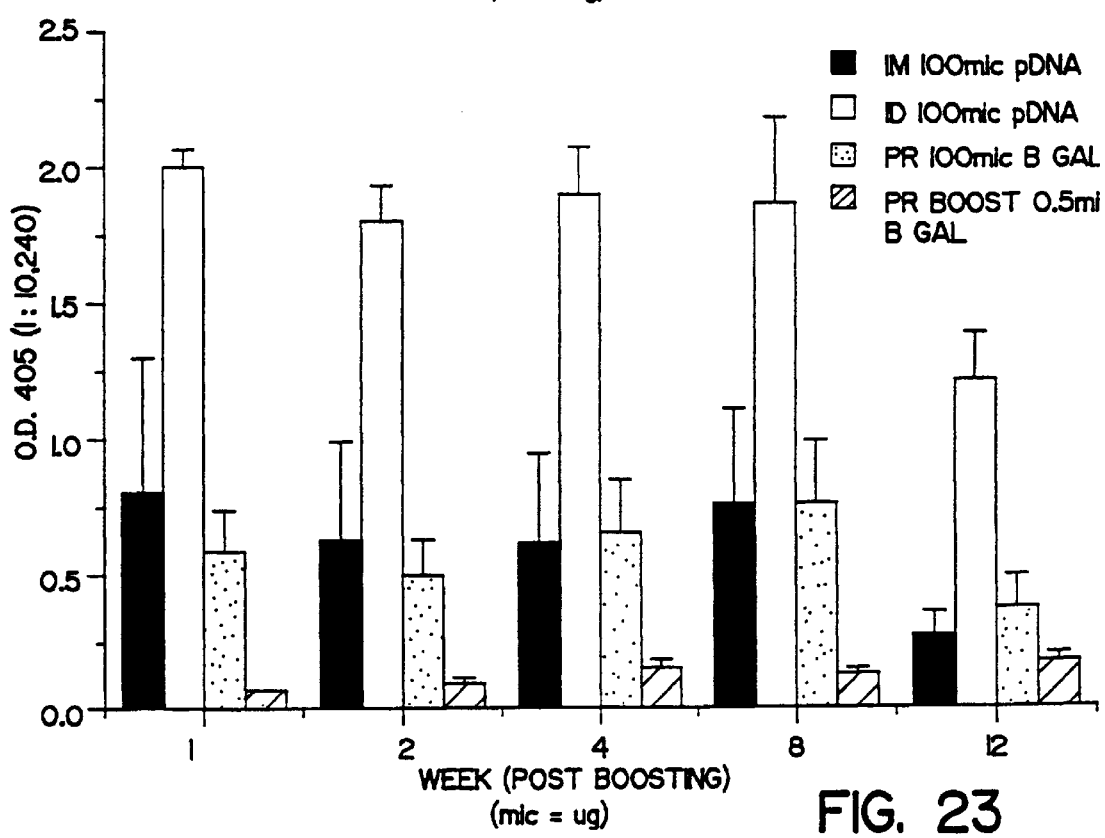

As shown in FIG. 23, it is clear that the animals which had received ID injections of pCMV Lac-Z plasmid had developed substantially better immunological memory than did animals which had received either IM injections of plasmid or of PR. Further, the memory which was developed by the ID injected animals persisted for a minimum of about 12 weeks.

EXAMPLE XVII

SELECTIVE INDUCTION OF A TH1 RESPONSE AFTER INTRADERMAL ADMINISTRATION OF NAKED POLYNUCLEOTIDES

In mice, IgG 2A antibodies are serological markers for a TH1 type immune response, whereas IgG 1 antibodies are indicative of a TH2 type immune response. TH2 responses include the allergy-associated IgE antibody class; soluble protein antigens tend to stimulate relatively strong TH2 responses. In contrast, TH1 responses are induced by antigen binding to macrophages and dendritic cells. TH1 responses are to be of particular importance in the treatment of allergies and AIDS.

To determine which response, if any, would be produced by mice who received naked polynucleotides according to the invention, mice were vaccinated with pCMV Lac-Z or protein as described in the preceding example. At 2 week intervals, any IgG 2a and IgG 1 to β-galactosidase were measured by enzyme-linked immunoabsorbent assay (using antibodies specific for the IgG 1 and IgG 2A subclasses) on microtiter plates coated with the enzyme.

Figure 24:
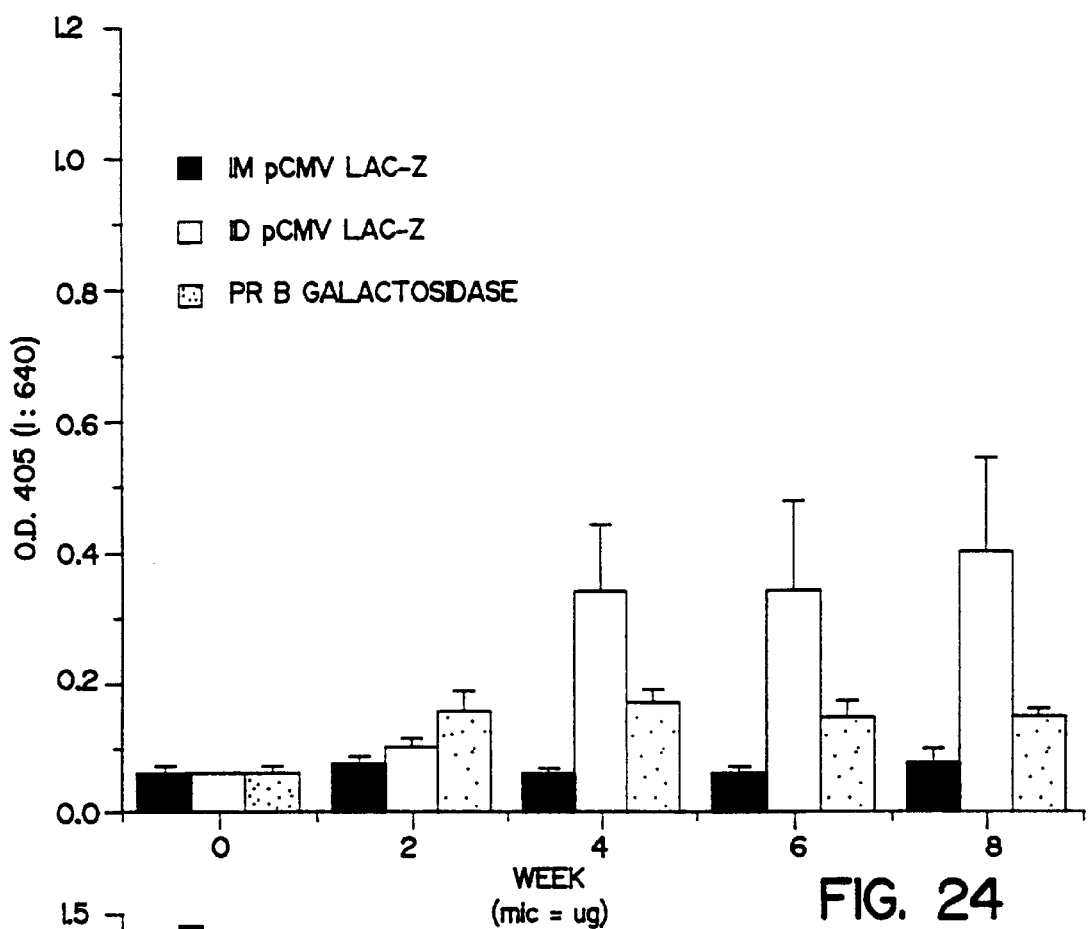
Figure 25:
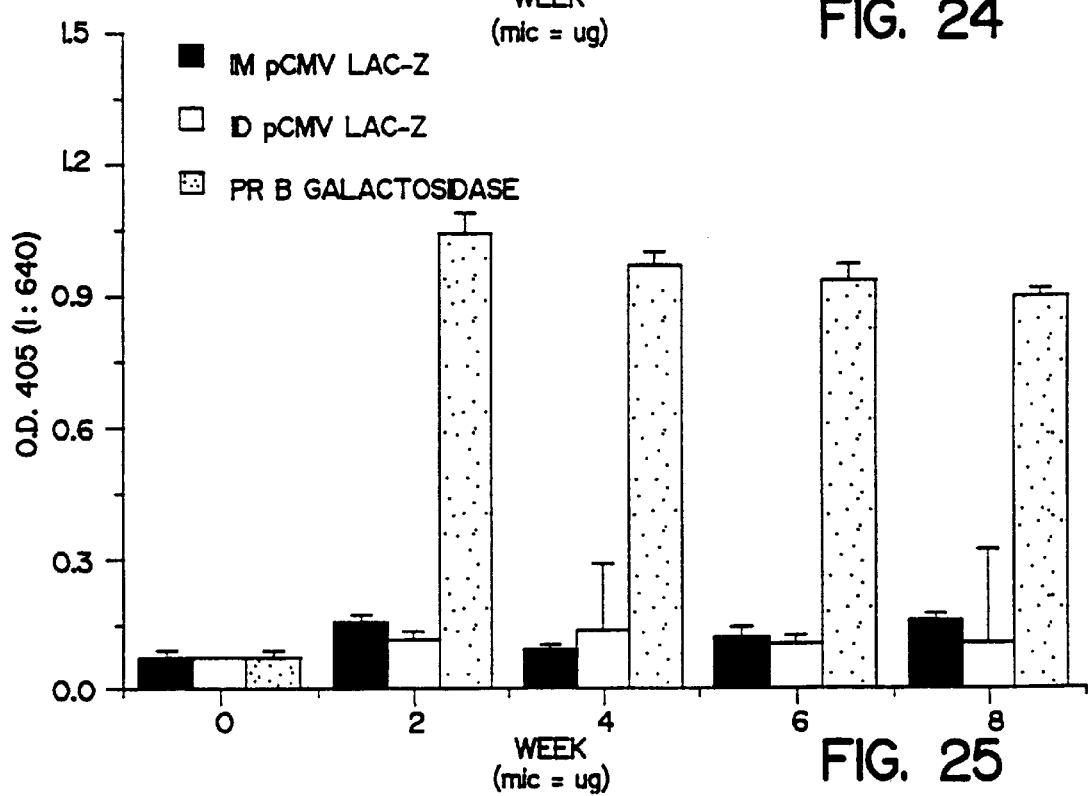
FIG. 25 depicts the results of an ELISA for IgG 1 type antibodies in sera for mice (1) injected intradermally or intramuscularly with a polynucleotide encoding β-galactosidase, or (2) the enzyme by intradermal injection.

As shown in FIG. 24, only the mice who received the plasmid by ID injection produced high titers of IgG 2A antibodies. As shown in FIG. 25, immunization of the mice with the enzyme itself ("PR") induced production of relatively high titers of IgG 1 antibodies. In the IM injected mice, low titers of both IgG 2A and IgG 1 antibodies were produced without apparent selectivity. The data shown in the FIGURES comprise averages of the values obtained from each group of 4 mice.

Figure 26:
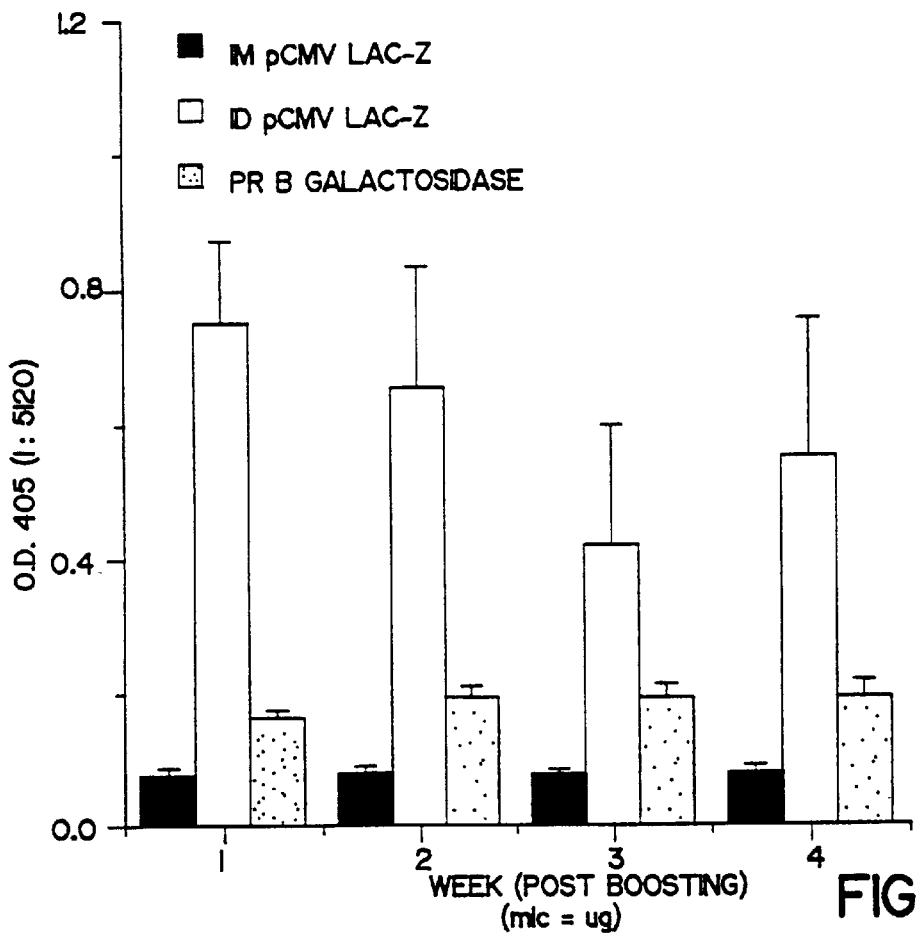
FIG. 26 depicts the results of an ELISA for IgG 2A type antibodies in sera of the mice described with respect to FIG. 25 after a booster injection of antigen.
Figure 27:
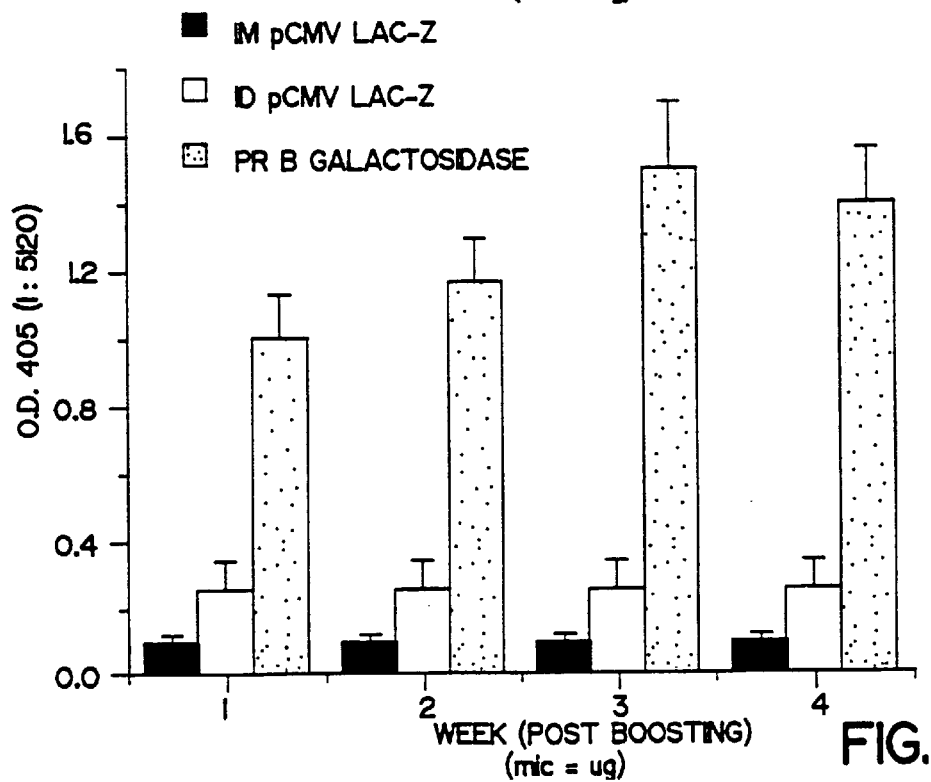
FIG. 27 depicts the results of an ELISA for IgG 1 type antibodies in sera of the mice described with respect to FIG. 24 after a booster injection of antigen.

To determine the stability of the antibody response over time, the same group of animals were boosted with 0.5 µg of enzyme injected intradermally. As shown in FIGS. 26 and 27 boosting of ID injection primed animals with the enzyme induced a nearly 10-fold rise in IgG 2A antibody responses (i.e., the antibody titer rose from 1:640 to 1:5120), but did not stimulate an IgG 1 response. These data indicate that the selective TH1 response induced by ID administration of naked polynudeotides is maintained in the host, despite subsequent exposure to antigen.

EXAMPLE XVIII

TH1 RESPONSES IN MICE AFTER ADMINISTRATION OF NAKED POLYNUCLEOTIDES WITH A MECHANICAL IRRITANT

The experiments described in Example XVII were repeated in separate groups of mice, except that (1) only a priming dose was tested, and (2) the pCMV Lac-Z plasmid was administered to one group of 4 mice using the tyne device described in Example X, while β-galactosidase protein (10 µg) was administered to another group of 4 mice by intradermal (ID) injection.

Figure 28:
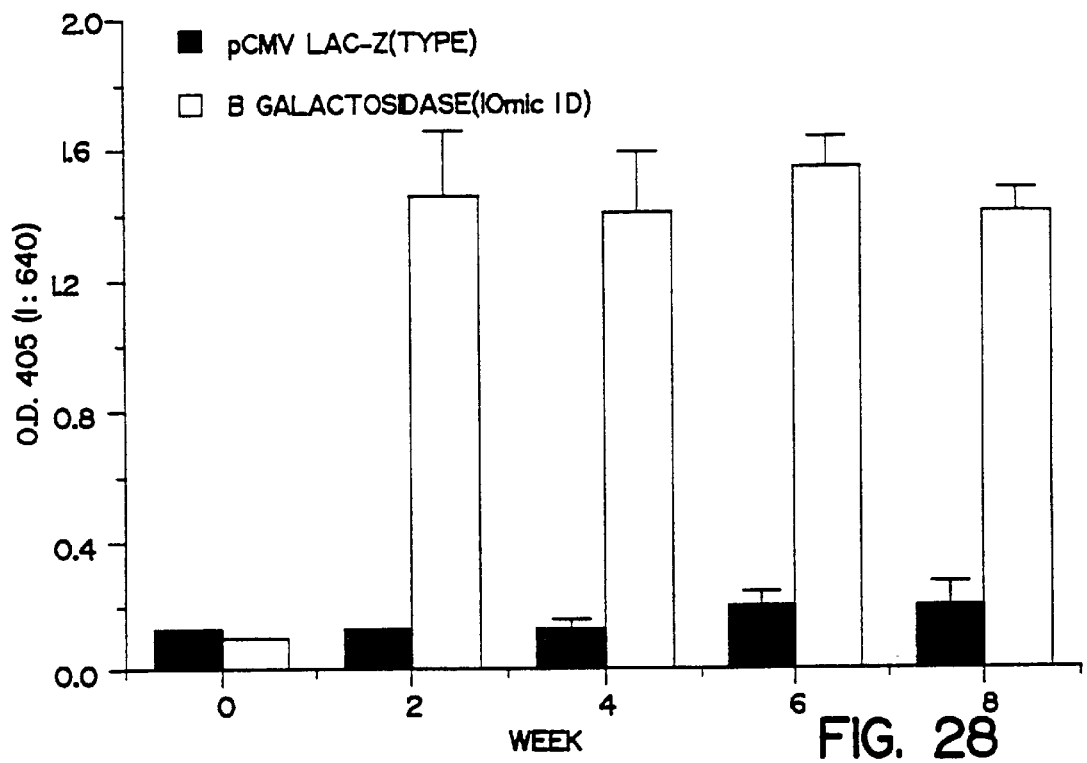
FIG. 28 depicts the results of an ELISA for IgG 2A type antibodies in sera for mice (1) introduced by scratching the skin with tynes coated with a polynucleotide encoding β-galactosidase, or (2) the enzyme by intradermal injection.
Figure 29:
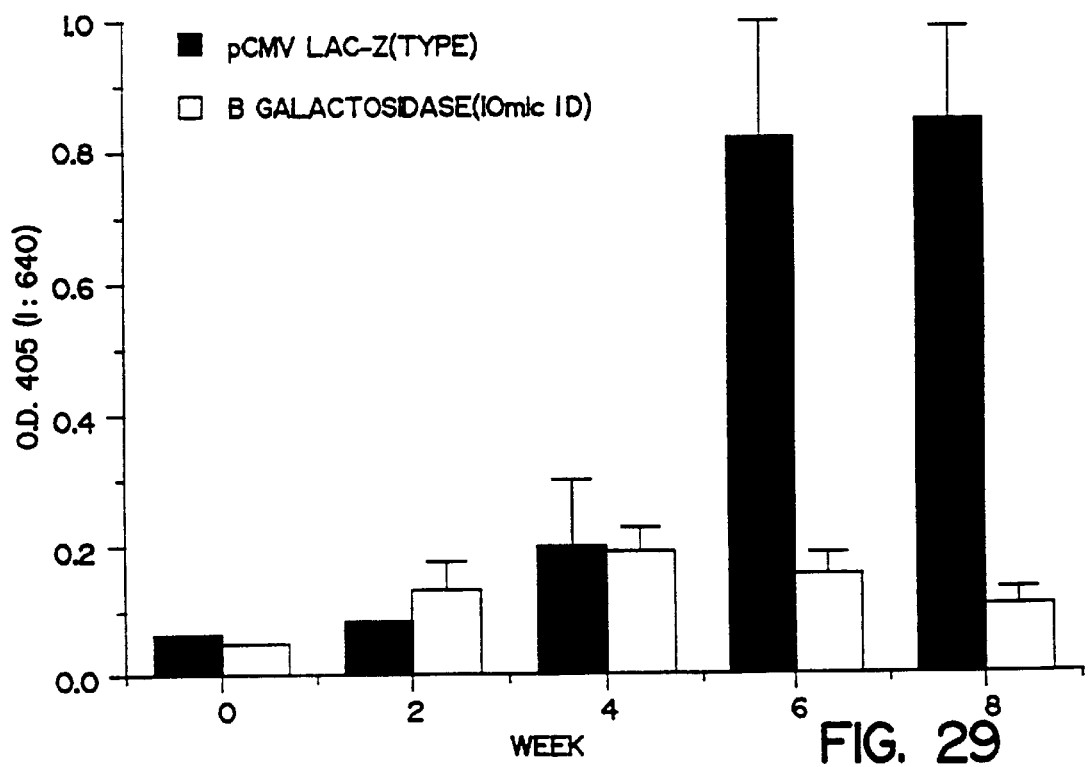
FIG. 29 depicts the results of an ELISA for IgG 1 type antibodies in sera for mice (1) introduced by scratching the skin with tynes coated with a polynucleotide encoding β-galactosidase, or (2) the enzyme by intradermal injection.

As shown in FIG. 28, the mice who received plasmid produced relatively low titers of IgG 1 antibody compared to the mice who received the protein. In contrast as shown in FIG. 29, the mice who received plasmid produced substantially higher titers of IgG 2A antibody as compared to the mice who received the protein.

These results are similar to those obtained in Example XVII except that, interestingly, the mice who received the plasmid via scratching of their skin with the tyne device produced even higher titers of IgG 2A antibody than did the mice who received the same plasmid via ID injection (both of which groups produced higher titers of IgG 2A antibody than did the mice who received the plasmid via IM injection). These results indicate that scratching of skin with the tyne device attracts greater number of APC's to the "injured" point of entry for the naked polynucleotides and are consistent with the theory that APC's are more efficient targets for gene administration and expression than are muscle or other somatic cells.

The data shown in the FIGURES comprise averages of the values obtained from each group of 4 mice.

We claim:

1. A composition of matter for epidermal administration of a polynucleotide into antigen presenting cells in the skin or mucosa of a host by scratching the skin or mucosa comprising:
   (a) mechanical irritant means for introducing the polynucleotide into the host, consisting of handle means to which a multiplicity of tynes are attached, wherein the tynes are as long as the expected thickness of the outermost layer of the host's epidermis or mucosal epithelia; and,
   (b) a polynucleotide in a pharmaceutically acceptable carrier, coated onto the tynes;
   wherein the polynucleotide operatively encodes an antigen for expression in the antigen presenting cells to stimulate a host Th1 type immune response to the antigen and is naked of any colloidal material which interferes with uptake of the polynucleotide by antigen presenting cells.

2. A composition of matter according to claim 1 wherein the carrier includes a chemical irritant to attract additional antigen presenting cells for uptake of the polynucleotide and expression of the antigen.

3. A composition of matter according to claim 2 wherein the chemical irritant consists essentially of a keratinolytic agent.

4. The composition according to claim 1 wherein the tynes are also coated with an immunostimulatory peptide.

5. The composition according to claim 1 wherein the polynucleotide further operatively encodes an immunostimulatory peptide.

* * * * *